(12) United States Patent
Villhauer

(10) Patent No.: US 6,432,969 B1
(45) Date of Patent: Aug. 13, 2002

(54) N-(SUBSTITUTED GLYCYL)-2 CYANOPYRROLIDINES, PHARMACEUTICAL COMPOSITIONS CONTAINING THEM AND THEIR USE IN INHIBITING DIPEPTIDYL PEPTIDASE-IV

(75) Inventor: Edwin Bernard Villhauer, Morristown, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/879,654

(22) Filed: Jun. 12, 2001

Related U.S. Application Data
(60) Provisional application No. 60/325,743, filed on Jun. 13, 2000.

(51) Int. Cl.$^7$ ............... C07D 237/24; C07D 403/06; C07D 401/12; A61K 31/50; A61P 29/00
(52) U.S. Cl. ............ 514/275; 548/540; 514/423; 514/343; 514/226; 546/279.1; 546/208; 544/332
(58) Field of Search ............ 548/540; 514/423, 514/343, 275, 326; 546/279.1, 208; 544/332

(56) References Cited

U.S. PATENT DOCUMENTS

| | | | |
|---|---|---|---|
| 6,011,155 A | | 1/2000 | Villhauer et al. ............ 544/333 |
| 6,124,305 A | * | 9/2000 | Villhauer ............ 514/272 |

FOREIGN PATENT DOCUMENTS

| | | |
|---|---|---|
| EP | 419683 | 4/1991 |
| WO | WO 95/15309 | 6/1995 |
| WO | WO 98/19998 | 5/1998 |
| WO | WO 00/34241 | 6/2000 |

OTHER PUBLICATIONS

Ashworth et al., "2–Cyanopyrrolidines as potent, stable inhibitors of dipeptidyl peptidase IV.", Bioorg.Med.Chem. Lett., vol. 6, No. 10, pp. 1163–1166, 1996.

Augustyns et al., "Pyrrolidines: Synthesis and structure–activity relationships as inhibitors of dipeptidyl peptidase IV.", Eur.J.Med.Chem., vol. 32, pp. 301–309, 1997.

Balkan et al., "Inhibition of dipeptidyl peptidase IV with NVP–DPP728 increases plasma GLP–1 (7–36 amide) concentrations and improves oral glucose tolerance in obese Zucker rats", Diabetologia, vol. 42, pp. 1324–1331, 1999.

Hughes et al., "NVP–DPP728 (1–[[[2–[(5–cyanopyridin–2–yl) amino] ethyl] amino] acetyl]–2–cyano–(S)–pyrrolidine), a slow–binding inhibitor of dipeptidyl peptidase IV.", Biochemistry, vol. 38, pp. 11597–11603, 1999.

Li et al., "Aminoacylpyrrolidine–2–nitriles: Potent and Stable inhibitors of dipeptidyl–peptidases.", Arch. Biochem. Biophys., vol. 323, No. 1, pp. 148–154, 1995.

Li et al., Arch. Biochem. Biophys., 323, 148–154, 1995.

Ashworth et al., Bioorg. Med. Chem. Lett., 6, 1163–1166, 1996.

Augustyns et al., Eur. J. Med. Chem., 32, 301–309, 1997.

Hughes et al., Biochemistry, 38, 11597–11603, 1999.

* cited by examiner

Primary Examiner—Mukund J. Shah
Assistant Examiner—Hong Liu
(74) Attorney, Agent, or Firm—Joseph J. Borovian

(57) ABSTRACT

The present invention relates to certain N-(substituted glycyl)-2-cyanopyrrolidines of formula I

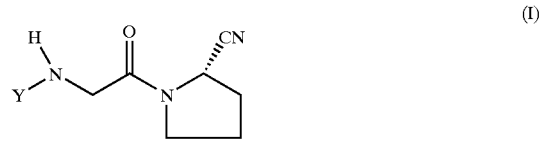

wherein Y is as defined herein, in free form or in acid addition salt form. Compounds of formula I inhibit DPP-IV (dipeptidyl-peptidase-IV) activity. They are therefore indicated for use as pharmaceuticals in inhibiting DPP-IV and in the treatment of conditions mediated by DPP-IV, such as non-insulin-dependent diabetes mellitus, arthritis, obesity, osteoporosis and further conditions of impaired glucose tolerance.

31 Claims, No Drawings

N-(SUBSTITUTED GLYCYL)-2 CYANOPYRROLIDINES, PHARMACEUTICAL COMPOSITIONS CONTAINING THEM AND THEIR USE IN INHIBITING DIPEPTIDYL PEPTIDASE-IV

This application claims the benefit of U.S. Provisional Application No. 60/325,743, filed Jun. 13, 2000, which was converted from U.S. application Ser. No. 09/592,336, and the contents of which are incorporated herein by reference.

FIELD OF THE INVENTION

The present invention relates to the area of dipeptidyl peptidase-IV inhibition and, more particularly, relates to certain N-(substituted glycyl)-2-cyanopyrrolidines, pharmaceutical compositions containing said compounds, and the use of said compounds in inhibiting dipeptidyl peptidase-IV.

1. Background of the Invention

Dipeptidyl peptidase-IV (DPP-IV) is a serine protease which cleaves N-terminal dipeptides from a peptide chain containing, preferably, a proline residue in the penultimate position. Although the biological role of DPP-IV in mammalian systems has not been completely established, it is believed to play an important role in neuropeptide metabolism, T-cell activation, attachment of cancer cells to the endothelium and the entry of HIV into lymphoid cells.

Likewise, it was discovered that DPP-IV is responsible for inactivating glucagon-like peptide-1 (GLP-1). Since GLP-1 is a major stimulator of pancreatic insulin secretion and has direct beneficial effects on glucose disposal, DPP-IV inhibition appears to represent an attractive approach for treating non-insulin-dependent diabetes mellitus (NIDDM).

2. Description of the Prior Art

WO95/15309 discloses certain peptide derivatives which are inhibitors of DPP-IV and, therefore, are useful in treating a number of DPP-IV mediated processes.

Archives of Biochemistry and Biophysics, Vol. 323, No. 1, pgs. 148–154 (1995) discloses certain aminoacylpyrrolidine-2-nitriles which are useful as DPP-IV inhibitors.

Bioorganic and Medicinal Chemistry Letters, Vol. 6, No. 10, pgs. 1163–1166 (1996) discloses certain 2-cyanopyrrolidines which are inhibitors of DPP-IV.

European Journal of Medicinal Chemistry, Vol. 32, pgs. 301–309 (1997) discloses certain pyrrolidides which are useful as DPP-IV inhibitors.

WO98/19998 discloses certain N-substituted-2-cyanopyrrolidines which are useful as DPP-IV inhibitors.

Biochemistry, Vol. 38, pgs. 11597–11603 (1999) discloses (1-[[[[2-[(5-cyanopyridin-2-yl)amino]ethyl]amino]acetyl]-2-cyano-(S)-pyrrolidine) as a slow-binding inhibitor of DPP-IV.

SUMMARY OF THE INVENTION

The present invention provides new DPP-IV inhibitors which are effective in treating conditions mediated by DPP-IV inhibition. More particularly, the present invention relates to certain N-(substituted glycyl)-2-cyanopyrrolidines which inhibit DPP-IV. In addition, the present invention provides pharmaceutical compositions useful in inhibiting DPP-IV comprising a therapeutically effective amount of a certain N-(substituted glycyl)-2-cyanopyrrolidine. Moreover, the present invention provides a method of inhibiting DPP-IV comprising administering to a mammal in need of such treatment a therapeutically effective amount of a certain N-(substituted glycyl)-2-cyanopyrrolidine.

DETAILED DESCRIPTION OF THE INVENTION

The essence of the instant invention is the discovery that certain N-(substituted glycyl)-2-cyanopyrrolidines are useful in inhibiting DPP-IV. In one embodiment, the present invention provides compounds of formula I:

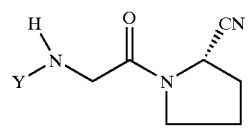

(I)

where Y is:

a) a group of the formula

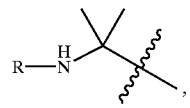

where R is an unsubstituted pyridine or pyrimidine ring; a pyridine or pyrimidine ring which is mono- or independently di-substituted by halo, trifluoromethyl, cyano, nitro or $C_{1-6}$alkyl; unsubstituted benzoyl; a benzoyl group which is mono- or di-substituted by halo or $C_{1-6}$alkyl; $C_{1-6}$alkylcarbonyl; di-$C_{1-6}$alkylaminocarbonyl; unsubstituted phenylaminocarbonyl; or a phenylaminocarbonyl group which is mono- or di-substituted on the phenyl ring by halo or $C_{1-6}$alkyl;

b) a group of the formula

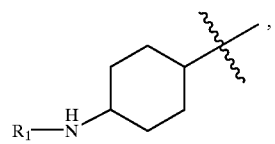

where $R_1$ is an unsubstituted pyridine, pyrimidine or phenyl ring; a pyridine, pyrimidine or phenyl ring which is mono- or independently di-substituted by halo, trifluoromethyl, cyano, nitro or $C_{1-6}$alkyl; an unsubstituted phenylsulfonyl group; a phenylsulfonyl group which is mono- or di-substituted on the phenyl ring by halo, trifluoromethyl, cyano, nitro or $C_{1-6}$alkyl; unsubstituted benzoyl; a benzoyl group which is mono- or di-substituted by halo or $C_{1-6}$alkyl; $C_{1-6}$alkylcarbonyl; thienyl sulfonyl; unsubstituted benzothiazole; or a benzothiazole group which is substituted on the phenyl ring by halo or $C_{1-6}$alkyl;

c) a group of the formula

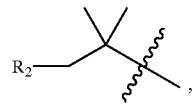

where $R_2$ is an unsubstituted phenyl ring; or a phenyl ring which is mono- or di-substituted by halo or $C_{1-6}$alkyl;

d) a group of the formula

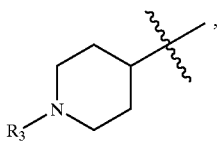

where R₃ is an unsubstituted phenylsulfonyl group; a phenylsulfonyl group which is mono- or di-substituted on the phenyl ring by halo, trifluoromethyl, cyano, nitro or $C_{1-6}$alkyl; $C_{1-6}$alkylcarbonyl; di-$C_{1-6}$alkylaminocarbonyl; $C_{3-8}$cycloalkylcarbonyl; unsubstituted benzoyl; a benzoyl group which is mono- or di-substituted by halo or $C_{1-6}$alkyl; unsubstituted phenylaminocarbonyl; phenylaminocarbonyl which is mono- or di-substituted on the phenyl ring by halo or $C_{1-6}$alkyl; a substituted thiazole ring; or a phenyl-substituted thiazole ring wherein the phenyl ring is mono- or di-substituted by halo or $C_{1-6}$alkoxy;

e) a (4-pentylbicyclo[2.2.2]oct-1-yl) amine group; or f) a group of the formula

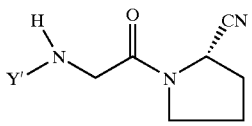

where R₄ is an unsubstituted phenyl ring; or a phenyl ring which is mono- or di-substituted by halo, trifluoromethyl, cyano, nitro or $C_{1-6}$alkyl; or an acid addition salt thereof.

Preferred compounds are those of formula Ia:

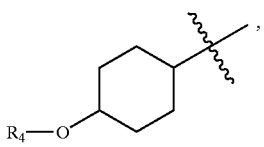

(Ia)

where Y' is:

a) a group of the formula

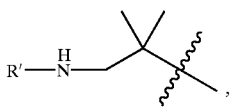

where R' is an unsubstituted pyridine or pyrimidine ring; a pyridine or pyrimidine ring which is mono- or independently di-substituted by halo, trifluoromethyl or cyano; unsubstituted benzoyl; a benzoyl group which is monosubstituted by halo or $C_{1-6}$alkyl; $C_{1-6}$alkylcarbonyl; di-$C_{1-6}$alkylaminocarbonyl; unsubstituted phenylaminocarbonyl; or a phenylaminocarbonyl group which is monosubstituted on the phenyl ring by halo or $C_{1-6}$alkyl;

b) a group of the formula

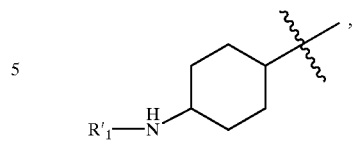

where R₁' is an unsubstituted pyridine, pyrimidine or phenyl ring; a pyridine, pyrimidine or phenyl ring which is monosubstituted by halo, trifluoromethyl, cyano, nitro or $C_{1-6}$alkyl; an unsubstituted phenylsulfonyl group; a phenylsulfonyl group which is monosubstituted on the phenyl ring by halo, trifluoromethyl, cyano, nitro or $C_{1-6}$alkyl; unsubstituted benzoyl; a benzoyl group which is monosubstituted by halo or $C_{1-6}$alkyl; $C_{1-6}$alkylcarbonyl; thienyl sulfonyl; unsubstituted benzothiazole; or a benzothiazole group which is substituted on the phenyl ring by halo or $C_{1-6}$alkyl;

c) a group of the formula

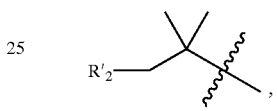

where R₂' is an unsubstituted phenyl ring; or a phenyl ring which is monosubstituted by halo or $C_{1-6}$alkyl;

d) a group of the formula

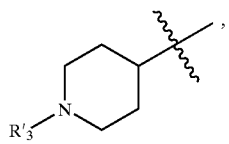

where R₃' is an unsubstituted phenylsulfonyl group; a phenylsulfonyl group which is monosubstituted on the phenyl ring by halo, trifluoromethyl, cyano, nitro or $C_{1-6}$alkyl; $C_{1-6}$alkylcarbonyl; di-$C_{1-6}$alkylaminocarbonyl; $C_{3-8}$cycloalkylcarbonyl; unsubstituted benzoyl; a benzoyl group which is monosubstituted by halo or $C_{1-6}$ alkyl; unsubstituted phenylaminocarbonyl; phenylaminocarbonyl which is monosubstituted on the phenyl ring by halo or $C_{1-6}$alkyl; a phenyl-substituted thiazole ring; or a phenyl-substituted thiazole ring wherein the phenyl ring is monosubstituted by halo or $C_{1-6}$alkoxy;

e) a (4-pentylbicyclo[2.2.2]oct-1-yl)amine group; or f) a group of the formula

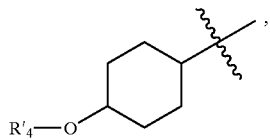

where R₄' is an unsubstituted phenyl ring; or a phenyl ring which is monosubstituted by halo, trifluoromethyl, cyano, nitro or $C_{1-6}$alkyl; or an acid addition salt thereof.

More preferred compounds are those of formula Ib:

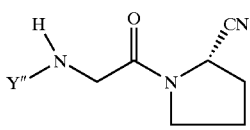

(Ib)

where Y" is:

a) a group of the formula

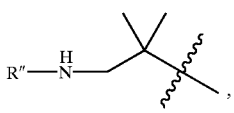

where R" is an unsubstituted pyridine or pyrimidine ring; a pyridine or pyrimidine ring which is mono-substituted by halo, trifluoromethyl or cyano or di-substituted by halo; unsubstituted benzoyl; a benzoyl group which is monosubstituted by halo or $C_{1-4}$alkyl; $C_{1-6}$alkylcarbonyl; di-$C_{1-6}$alkylaminocarbonyl; unsubstituted phenylaminocarbonyl; or a phenylaminocarbonyl group which is monosubstituted on the phenyl ring by halo or $C_{1-4}$alkyl;

b) a group of the formula

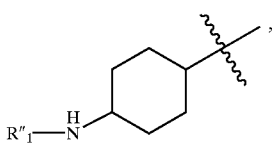

where $R_1"$ is an unsubstituted pyridine, pyrimidine or phenyl ring; a pyridine, pyrimidine or phenyl ring which is monosubstituted by halo, trifluoromethyl, cyano, nitro or $C_{1-4}$alkyl; an unsubstituted phenylsulfonyl group; a phenylsulfonyl group which is monosubstituted on the phenyl ring by halo, trifluoromethyl, cyano, nitro or $C_{1-4}$alkyl; unsubstituted benzoyl; a benzoyl group which is monosubstituted by halo or $C_{1-4}$alkyl; $C_{1-6}$alkylcarbonyl; thienyl sulfonyl; unsubstituted benzothiazole; or a benzothiazole group which is substituted on the phenyl ring by halo or $C_{1-4}$alkyl;

c) a group of the formula

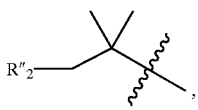

where $R_2"$ is an unsubstituted phenyl ring; or a phenyl ring which is monosubstituted by halo or $C_{1-4}$ alkyl;

d) a group of the formula

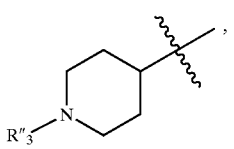

where $R_3"$ is an unsubstituted phenylsulfonyl group; a phenylsulfonyl group which is monosubstituted on the phenyl ring by halo, trifluoromethyl, cyano, nitro or $C_{1-4}$alkyl; $C_{1-6}$alkylcarbonyl; di-$C_{1-6}$alkylaminocarbonyl; $C_{3-8}$cycloalkylcarbonyl; unsubstituted benzoyl; a benzoyl group which is monosubstituted by halo or $C_{1-4}$alkyl; unsubstituted phenylaminocarbonyl; phenylaminocarbonyl which is monosubstituted on the phenyl ring by halo or $C_{1-4}$alkyl; a phenyl-substituted thiazole ring; or a phenyl-substituted thiazole ring wherein the phenyl ring is monosubstituted by halo or $C_{1-4}$alkoxy;

e) a (4-pentylbicyclo[2.2.2]oct-1-yl)amine group; or f) a group of the formula

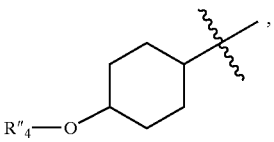

where $R_4"$ is an unsubstituted phenyl ring; or a phenyl ring which is monosubstituted by halo, trifluoromethyl, cyano, nitro or $C_{1-4}$alkyl;

or an acid addition salt thereof.

Even more preferred compounds are those of formula Ic:

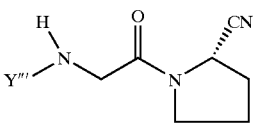

(Ic)

where Y'" is:

a) a group of the formula

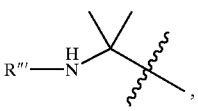

where R'" is an unsubstituted pyridine or pyrimidine ring; a pyridine or pyrimidine ring which is monosubstituted by chloro, trifluoromethyl or cyano or disubstituted by chloro; unsubstituted benzoyl; a benzoyl group which is monosubstituted by chloro, methyl or ethyl; $C_{1-6}$alkylcarbonyl; di-$C_{1-6}$alkylaminocarbonyl; unsubstituted phenylaminocarbonyl; or a phenylaminocarbonyl group which is monosubstituted on the phenyl ring by chloro;

b) a group of the formula

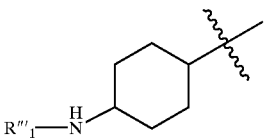

where $R_1'''$ is an unsubstituted pyridine, pyrimidine or phenyl ring; a pyridine, pyrimidine or phenyl ring which is monosubstituted by chloro, trifluoromethyl or cyano; an unsubstituted phenylsulfonyl group; a phenylsulfonyl group which is monosubstituted on the phenyl ring by chloro or trifluoromethyl; unsubstituted benzoyl; a benzoyl group which is monosubstituted by chloro; $C_{1-6}$alkylcarbonyl; thienyl sulfonyl; unsubstituted benzothiazole; or a benzothiazole group which is substituted on the phenyl ring by chloro;

c) a group of the formula

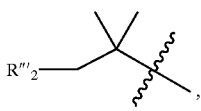

where $R_2'''$ is an unsubstituted phenyl ring; or a phenyl ring which is monosubstituted by fluoro;

d) a group of the formula

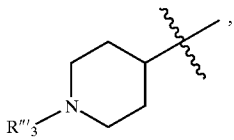

where $R_3'''$ is an unsubstituted phenylsulfonyl group; a phenylsulfonyl group which is monosubstituted on the phenyl ring by chloro or trifluoromethyl; $C_{1-6}$alkylcarbonyl; di-$C_{1-6}$alkylaminocarbonyl; $C_{3-8}$cycloalkylcarbonyl; unsubstituted benzoyl; a benzoyl group which is monosubstituted by chloro; unsubstituted phenylaminocarbonyl; phenylaminocarbonyl which is monosubstituted on the phenyl ring by chloro; a phenyl-substituted thiazole ring; or a phenyl-substituted thiazole ring wherein the phenyl ring is monosubstituted by chloro or methoxy;

e) a (4-pentylbicyclo[2.2.2]oct-1-yl)amine group; or f) a group of the formula

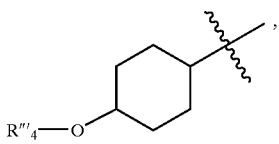

where $R_4'''$ is an unsubstituted phenyl ring; or a phenyl ring which is monosubstituted by chloro or trifluoromethyl;

or an acid addition salt thereof.

Compounds of formula I, Ia, 1b or Ic, wherein Y represents a group of formula b) and f) are preferably in the trans orientation that is represented by formulae (I-b)

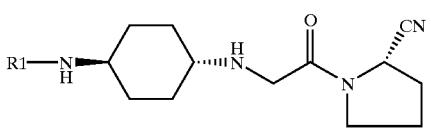

(I-b')

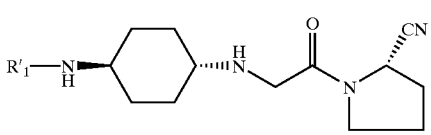

(I-b")

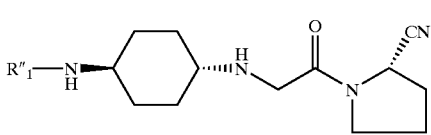

-continued (I-b''')

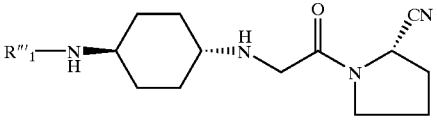

(I-f)

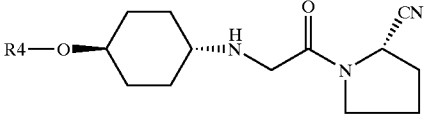

(I-f')

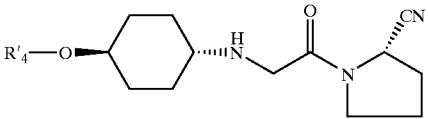

(I-f")

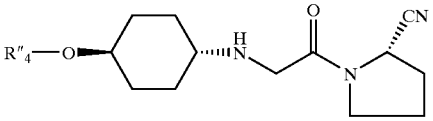

and (I-f''')

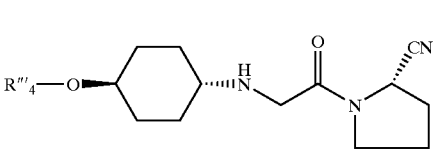

In another embodiment, the instant invention provides pharmaceutical compositions useful in inhibiting DPP-IV comprising a pharmaceutically acceptable carrier or diluent and a therapeutically effective amount of a compound of formula I above, or a pharmaceutically acceptable acid addition salt thereof, preferably a compound of formula Ia above, or a pharmaceutically acceptable acid addition salt thereof, more preferably a compound of formula Ib above, or a pharmaceutically acceptable acid addition salt thereof, and even more preferably a compound of formula Ic above, or a pharmaceutically acceptable acid addition salt thereof.

In still another embodiment, the instant invention provides a method of inhibiting DPP-IV comprising administering to a mammal in need of such treatment a therapeutically effective amount of a compound of formula I above, or a pharmaceutically acceptable acid addition salt thereof, preferably a compound of formula Ia above, or a pharmaceutically acceptable acid addition salt thereof, more preferably a compound of formula Ib above, or a pharmaceutically acceptable acid addition salt thereof, and even more preferably a compound of formula Ic above, or a pharmaceutically acceptable acid addition salt thereof.

In a further embodiment, the instant invention provides a method of treating conditions mediated by DPP-IV inhibition comprising administering to a mammal in need of such treatment a therapeutically effective amount of a compound of formula I above, or a pharmaceutically acceptable acid addition salt thereof, preferably a compound of formula Ia above, or a pharmaceutically acceptable acid addition salt thereof, more preferably a compound of formula Ib above, or a pharmaceutically acceptable acid addition salt thereof, and even more preferably a compound of formula Ic above, or a pharmaceutically acceptable acid addition salt thereof.

The compounds of formula I can exist in free form or in acid addition salt form. Pharmaceutically acceptable (i.e., non-toxic, physiologically acceptable) salts are preferred, although other salts are also useful, e.g., in isolating or purifying the compounds of this invention. Although the preferred acid addition salts are the hydrochlorides, salts of methanesulfonic, sulfuric, phosphoric, citric, lactic and acetic acid may also be utilized.

The compounds of the invention may exist in the form of optically active isomers or diastereoisomers and can be separated and recovered by conventional techniques, such as chromatography.

Listed below are definitions of various terms used to describe this invention. These definitions apply to the terms as they are used throughout this specification, unless otherwise limited in specific instances, either individually or as part of a larger group.

The term "halo" refers to chloro, fluoro, bromo or iodo.

The term "$C_{1-6}$alkyl" and the "$C_{1-6}$alkyl" portion of "di-$C_{1-6}$alkylaminocarbonyl" refers to straight or branched chain hydrocarbon groups having 1 to 6 carbon atoms, preferably 1 to 4 carbon atoms, more preferably 1 or 2 carbon atoms. Exemplary alkyl groups include methyl, ethyl, propyl, isopropyl, n-butyl, t-butyl, isobutyl, pentyl, hexyl and the like.

The "$C_{1-6}$alkyl" portion of "$C_{1-6}$alkylcarbonyl", in addition to the definition above, also refers to cyclic hydrocarbon groups, e.g. cyclopropyl, cyclobutyl, cyclopentyl and cyclohexyl.

The $C_{3-8}$ portion of $C_{3-8}$cycloalkylcarbonyl refers to e.g. cyclopropyl, cyclobutyl, cyclopentyl and cyclohexyl.

The bond containing the wavy line signifies the point of attachment of the "Y" group to the glycyl-2-cyanopyrrolidine moiety.

The N-(substituted glycyl)-2-cyanopyrrolidines of the invention may be prepared, e.g., by a process which comprises coupling a reactive (2-cyanopyrrolidine) carbonylmethylene compound with an appropriate substituted amine. More particularly, the compounds of formula I may be prepared by reacting a compound of formula II

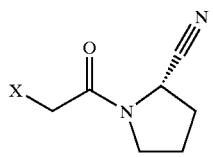

II where X is a reactive group (preferably a halogen group such as chlorine, bromine or iodine, more preferably chlorine) with a compound of formula III

Y—NH$_2$  III where Y is as defined above, and recovering the resultant compound of formula I in free form or in acid addition salt form.

The coupling may be effected by reacting the compound of formula II with 1 to 3 equivalents, preferably 3 equivalents, of a primary amine compound of formula III. The reaction is conveniently conducted in the presence of an inert, organic solvent, preferably a chlorinated, aliphatic hydrocarbon such as methylene chloride or a cyclic ether such as tetrahydrofuran, at a temperature of from about 0° to about 35° C., preferably from about 0° to about 25° C.

The compounds of the invention may be isolated from the reaction mixture and purified in conventional manner, e.g., by chromatography.

The starting compounds of formula II may be prepared by the following two-step reaction:

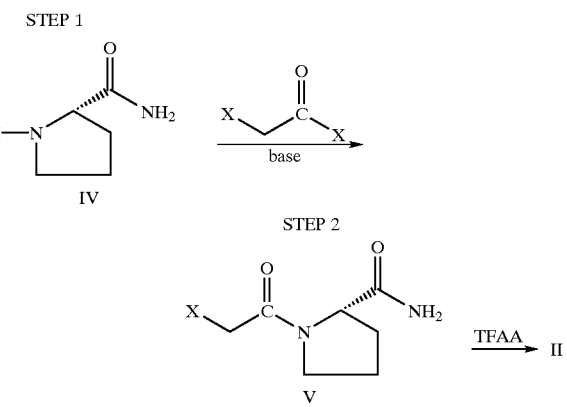

where X is as defined above.

Step 1 involves the reaction of the L-prolinamide compound of formula IV with a slight molar excess of a haloacetylhalide such a chloroacetylchloride or bromoacetylbromide and a base, e.g., an inorganic base such as potassium carbonate or an organic base such as triethylamine. The reaction is conveniently conducted in the presence of an inert, organic solvent, preferably a cyclic ether such as tetrahydrofuran or a chlorinated aliphatic hydrocarbon such as methylene chloride at a temperature of from about 0° to about 25° C., preferably from about 0° to about 15° C.

Step 2 concerns the dehydration of the compound prepared in Step 1, i.e, a en compound of formula V, with 1 to 2 equivalents of trifluoroacetic anhydride (TFAA) to obtain a compound of formula II. The dehydration is conveniently conducted in the presence of an inert, organic solvent, preferably a cyclic ether such as tetrahydrofuran or a chlorinated, aliphatic hydrocarbon such as methylene chloride, at a temperature of from about 0° to about 25° C., preferably from about 0° to about 15° C.

Insofar as their preparation is not particularly described herein, the primary amine compounds of formula III are either known or may be prepared from known compounds in a known manner or analogously to known methods or analogously to methods described in the Examples. For example, the amine compounds of formula III may be prepared by reacting excess 1,2-diamino-2-methylpropane with the appropriate chloropyridine, chloropyrimidine, acid chloride, carbamoyl chloride or sulfonyl chloride. Thus, 2-[(5-chloro-2-pyridinyl)amino]-1,1-dimethylamine can be prepared by refluxing 2,5-dichloropyridine in excess 1,2-diamino-2-methylpropane for a period of between 2 and 12 hours. The following amines can be prepared in a similar fashion: a) 2-[(5-cyano-2-pyridinyl)amino]-1,1-dimethylethylamine from 5-cyano-2-chloropyridine, b) 2-[(5-trifluoromethyl-2-pyridinyl)amino]-1,1-dimethylethylamine from 5-trifluoromethyl-2-chloropyridine, c) 2-[(3-chloro-2-pyridinyl)amino]-1,1-dimethylethylamine from 2,3-dichloropyridine, d) 2-[(3,5-dichloro-2-pyridinyl)amino]-1,1-dimethylethylamine from 2,3,5-trichloropyridine, and e) 2-[(3-trifluoromethyl-2-pyridinyl)amino]-1,1-dimethylethylamine from 2-chloro-3-trifluoromethyl pyridine. The following amines can be prepared in a similar fashion at room temperature or lower, in the presence of an organic solvent, such as tetrahydrofuran and a base, such as potassium carbonate: a) 2-[(4-methylbenzoyl)amino]-1,1-dimethylethylamine from p-toluoyl chloride, b) 2-[(4-trifluoromethyl-2-pyridinyl) amino-1,1-dimethylethylamine from 2-chloro-4-

(trifluoromethyl)pyridine, c) 2-[(2,2-dimethyl-1-oxopropyl) amino]-1,1-dimethylethyl]amine from trimethylacetyl chloride, d) 2-[(4-chlorobenzoyl)amino]-1,1-dimethylethylamine from 4-chlorobenzoyl chloride, e) 2-[[(diisopropylamino)carbonyl]amino]-1,1-dimethylethylamine from diisopropylcarbamylchloride, and f) 2-[[[(4-chlorophenyl)amino]carbonyl]amino]-1,1-dimethylethylamine from 4-chlorophenyl isocyanate. In addition, the amine compounds of formula III may be prepared by reacting excess trans-1,4-diaminocyclohexane with the appropriate chloropyridine, chloropyrimidine, acid chloride, carbamoyl chloride, chlorobenzothiazole or sulfonyl chloride. For example, 1-[4-[(5-cyano-2-pyridinyl) amino]cyclohexylamine can be prepared from 5-cyano-2-chloropyridine and two equivalents of 1,4-diaminohexane at room temperature in the presence of an organic solvent, such as dioxane and a base, such as potassium carbonate, for a period of between 2 and 48 hours. The following amines can be prepared in a similar fashion: a) 1-[4-[(phenylsulfonyl) amino]cyclohexyl]amine from phenylsulfonyl chloride, b) 1-[4-(benzoylamino)cyclohexyl]amine from benzoylchloride, c) 1-[4-[[(4-trifluoromethyl)-2-pyrimidinyl]amino]cyclohexyl]amine from 2-chloro-4-(trifluoromethyl)pyrimidine, d) 1-[4-[[(3-trifluoromethyl)-2-pyridinyl)amino]cyclohexyl]amine from 3-trifluoromethyl-2-chloropyridine, e) 1-[[4-[(4-chlorophenyl)sulfonyl]amino]cyclohexyl]amine from 4-chlorobenzenesulfonyl chloride, f) 1-[4-[(5-trifluoromethyl-2-pyridinyl)amino]cyclohexyl]amine from 5-trifluoromethyl-2-chloropyridine, g)1-[4-[(2-chloro-4-pyrimidinyl)amino]cyclohexyl]amine from 2,4dichloropyrimidine, h) 1-[4-[(4-chlorobenzoyl)amino] cyclohexyl]amine from 4-chlorobenzoyl chloride, i) 1-[4-[(2,2-dimethyl-1-oxopropyl)amino]cyclohexyl]amine from trimethylacetyl chloride, j) 1-[4-[(2-benzothiazolyl)amino] cyclohexyl]amine from 2-chlorobenzothiazole in THF at reflux for 18 hr., k) 1-[4-[(4-cyanophenyl)amino] cyclohexyl]amine from 4-aminobenzonitrile in DMF at 100° C. for 48 hours, l) 1-[4-[(cyclohexylcarbonyl)amino] cyclohexyl]amine from cyclohexanecarbonyl chloride, m) 1-[4-[(5-chloro-2-benzothiazolyl)amino]cyclohexyl]amine from 5-chloro-2-mercaptobenzothiazole at >200° C. for 1 hr in 1,4-diaminocyclohexane as solvent, n) 1-[4-[(4-trifluoromethyl)phenyl]sulfonyl]amino]cyclohexyl]amine from 4-(trifluoromethyl)benzenesulfonyl chloride, and o) 1-[4-[[(2-thienyl)sulfonyl]amino]cyclohexyl]amine from 2-(thienyl)sulfonyl chloride. Moreover, the amine compounds of formula III may be prepared by reacting trans-4-aminocyclohexanol with the appropriate chloropyridine, chloropyrimidine, acid chloride, carbamoyl chloride, chlorobenzothiazole or sulfonyl chloride. For example, 1-[4-[4-(trifluoromethyl)phenoxy]cyclohexyl]amine can be prepared by slowly adding 4-fluorobenzotrifluoride (1.25 equivalents) to a suspension of sodium hydride (3.00 equivalents) and trans-4-aminocyclohexanol (1.00 equivalent) in DMF. The desired amine is obtained after stirring for three hours at 60° C. and then at room temperature for 18 hours. The following amines can be prepared in a similar fashion: a) 1-[4-[4-(chlorophenoxy)]cyclohexyl] amine from 1-chloro-4-fluorobenzene, b) 1-[4-[(3-trifluoromethyl)phenoxy]cyclohexyl]amine from 1-fluoro-3-trifluoromethylbenzene, and c) 1-[4-(3-chlorophenoxy) cyclohexyl]amine from 1-chloro-3-fluorobenzene. Furthermore, the amine compounds of formula III may be prepared by reacting tert-butyl-4-piperidylcarbamate with isocyanates and carbamyl chlorides followed by tert-butylcarbamate deprotection. For example, 1-[1-[[(4-chlorophenyl)amino]carbonyl]-4-piperidinyl]amine, monohydrochloride can be prepared with the addition of 4-chlorophenyl isocyanate (1.00 equivalent) to a solution of tert-butyl-4-piperidylcarbamate (1.00 equivalent) in tetrahydrofuran followed by stirring at ice water temperature for two hours, followed by deprotection of the resulting urea (hydrogen chloride in ethyl acetate). 1-[1-[(diisopropylamino)carbonyl]-4-piperidinyl]amine can be prepared in a similar fashion from diisopropylcarbamyl chloride. Still further, the amine compounds of formula III may be prepared from ted-butyl-4-piperidylcarbamate to provide 1-[1-[4-(4-Z-phenyl)-2-thiazolyl]-4-piperidinyl] amines where Z is either H, Cl or methoxy. For example, 1-[1-[4-(4-methoxyphenyl)-2-thiazolyl]-4-piperidinyl] amine, monohydride can be prepared with the addition of benzoyl isothiocyanate (1.00 equivalent) to a solution of tert-butyl-4-piperidylcarbamate (1.00 equivalent) in tetrahydrofuran followed by stirring at room temperature for two hours. Hydrolysis of the resulting benzoyl isothiocyanate ($K_2CO_3/H_2O$, reflux for 24 h) provides the thiourea which is reacted with 1.00 equivalent of 2-bromo-4'-methoxyacetophenone (EtOH, $NEt_3$ at reflux for 2 hours). Deprotection of the t-butylcarbamate protecting group (hydrogen chloride in ethyl acetate) provides the target amine monohydrochloride. The following amines can be prepared in a similar fashion: a) 1-[1-(4-phenyl-2-thiazolyl)-4-piperidinyl]amine from 2-bromoacetophenone, and b) 1-[1-[4-chlorophenyl)-2-thiazolyl]-4-piperidinyl]amine from 2-bromo-4'-chloroacetophenone.

The compounds of formula I having basic groups can be converted into acid addition salts, especially pharmaceutically acceptable acid addition salts. For example, the free base of a compound of formula I can be reacted with hydrochloric acid in gaseous form to form the corresponding mono- and di-hydrochloride salt forms, whereas reacting the free base with methanesulfonic acid forms the corresponding mesylate salt form. All pharmaceutically acceptable acid addition salt forms of the compounds of formula I are intended to be embraced by the scope of this invention.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

As indicated above, all of the compounds of formula I, and their corresponding pharmaceutically acceptable acid addition salts, are useful in inhibiting DPP-IV. The ability of the compounds of formula I, and their corresponding pharmaceutically acceptable acid addition salts, to inhibit DPP-IV may be demonstrated employing the Caco-2 DPP-IV Assay which measures the ability of test compounds to inhibit DPP-IV activity from human colonic carcinoma cell extracts. The human colonic carcinoma cell line Caco-2 was obtained from the American Type Culture Collection (ATCC HTB 37). Differentiation of the cells to induce DPP-IV expression was accomplished as described by Reisher, et al. in an article entitled "Increased expression of intestinal cell line Caco-2" in Proc. Natl. Acad. Sci., Vol. 90, pgs. 5757–5761 (1993). Cell extract is prepared from cells solubilized in 10 mM Tris HCl, 0.15 M NaCl, 0.04 t.i.u.aprotinin, 0.5% nonidet-P40, pH 8.0, which is centrifuged at 35,000 g for 30 min. at 4° C. to remove cell debris. The assay is conducted by adding 20 µg solubilized Caco-2 protein, diluted to a final volume of 125 µl in assay buffer (25 mM Tris HCl pH 7.4, 140 mM NaCl, 10 mM KCl, 1% bovine serum albumin) to microtiter plate wells. After a 60 min. incubation at room temperature, the reaction is initiated by adding 25 μl of 1 mM substrate (H-Alanine-Proline-pNA; pNA is p-nitroaniline). The reaction is carried out at room temperature for 10 minutes after which time a 19 μl volume of 25% glacial acetic acid is added to stop the reaction. Test compounds are typically added as 30 μl additions and the assay buffer volume is reduced to 95 μl. A standard curve of free p-nitroaniline is generated using 0–500 μM solutions of free pNA in assay buffer. The curve generated is linear and is used for interpolation of substrate consumption (catalytic activity in nmoles substrate cleaved/min). The endpoint is determined by measuring absorbance at 405 nm in a Molecular Devices UV Max microtiter plate reader.

The potency of the test compounds as DPP-IV inhibitors, expressed as $IC_{50}$, is calculated from 8-point, dose-response curves using a 4-parameter logistic function.

The following $IC_{50}$'s were obtained:

| Compound | Caco-2 DPP-IV (nM) |
|---|---|
| Ex. 1 | 2 |
| Ex. 2A | 2 |
| Ex. 2B | 5 |
| Ex. 2C | 99 |
| Ex. 2D | 44 |
| Ex. 2E | 27 |
| Ex. 2F | 45 |
| Ex. 2G | 270 |
| Ex. 2H | 79 |
| Ex. 2I | 80 |
| Ex. 2J | 41 |
| Ex. 2K | 56 |
| Ex. 2L | 3 |
| Ex. 2M | 34 |
| Ex. 2N | 5 |
| Ex. 2O | 8 |
| Ex. 2P | 15 |
| Ex. 2Q | 30 |
| Ex. 2R | 4 |
| Ex. 2S | 3 |
| Ex. 2T | 31 |
| Ex. 2U | 39 |
| Ex. 2V | 9 |
| Ex. 2W | 13 |
| Ex. 2X | 22 |
| Ex. 2Y | 12 |
| Ex. 2Z | 66 |
| Ex. 2AA | 56 |
| Ex. 2BB | 19 |
| Ex. 2CC | 29 |
| Ex. 2DD | 156 |
| Ex. 2EE | 23 |
| Ex. 2FF | 15 |
| Ex. 2GG | 22 |
| Ex. 2HH | 18 |
| Ex. 2II | 44 |
| Ex. 2JJ | 94 |
| Ex. 2KK | 28 |
| Ex. 2LL | 61 |
| Ex. 2MM | 22 |
| Ex. 3 | 124 |
| Ex. 4A | 24 |
| Ex. 4B | 35 |
| Ex. 4C | 83 |
| Ex. 4D | 114 |
| Ex. 5 | 36 |

The ability of the compounds of formula I, and their corresponding pharmaceutically acceptable acid addition salts, to inhibit DPP-IV may also be demonstrated by measuring the effects of test compounds on DPP-IV activity in human and rat plasma employing a modified version of the assay described by Kubota, et al. in an article entitled "Involvement of dipeptidylpeptidase IV in an in vivo immune response" in Clin. Exp. Immunol., Vol. 89, pgs. 192–197 (1992). Briefly, 5 μl of plasma are added to 96-well flat-bottom micortiter plates (Falcon), followed by the addition of 5 μl of 80 mM $MgCl_2$ in incubation buffer (25 mMHEPES, 140 mM NaCl, 1% RIA-grade BSA, pH 7.8). After a 60 min. incubation at room temperature, the reaction is initiated by the addition of 10 μl of incubation buffer containing 0.1 mM substrate (H-Glycine-Proline-AMC; AMC is 7-amino 4-methylcoumarin). The plates are covered with aluminum foil (or kept in the dark) and incubated at room temperature for 20 min. After the 20 min. reaction, florescence is measured using a CytoFluor 2350 fluorimeter (Excitation 380 mn Emission 460 nm; sensitivity setting 4). Test compounds are typically added as 2 μl additions and the assay buffer volume is reduced to 13 μl. A fluorescence-concentration curve of free AMC is generated using 0–50 μM solutions of AMC in assay buffer. The curve generated is linear and is used for interpolation of substrate consumption (catalytic activity in nmoles substrate cleaved/min). As with the previous assay, the potency of the test compounds as DPP-IV inhibitors, expressed as $IC_{50}$, is calculated from 8-point, dose-response curves using a 4 parameter logistic function.

The following $IC_{50}$'s were obtained:

| Compound | Human Plasma DPP-IV (nM) | Rat Plasma DPP-IV (nM) |
|---|---|---|
| Ex. 1 | 30 | 6 |
| Ex. 2A | 10 | 5 |
| Ex. 2B | 59 | 11 |
| Ex. 2C | 50 | 25 |
| Ex. 2D | 93 | 71 |
| Ex. 2E | 27 | 19 |
| Ex. 2F | 46 | 37 |
| Ex. 2G | 153 | 111 |
| Ex. 2H | 79 | 46 |
| Ex. 2I | 73 | 31 |
| Ex. 2J | 421 | 49 |
| Ex. 2K | 305 | 38 |
| Ex. 2L | 9 | 4 |
| Ex. 2M | 10 | 6 |
| Ex. 2N | 10 | 5 |
| Ex. 2O | 8 | 9 |
| Ex. 2P | 16 | 11 |
| Ex. 2Q | 38 | 38 |
| Ex. 2R | 23 | 15 |
| Ex. 2S | 4 | 2 |
| Ex. 2T | 26 | 37 |
| Ex. 2U | 27 | 14 |
| Ex. 2V | 28 | 11 |
| Ex. 2W | 19 | 7 |
| Ex. 2X | 47 | 20 |
| Ex. 2Y | 124 | 37 |
| Ex. 2Z | 122 | 88 |
| Ex. 2AA | 33 | 16 |
| Ex. 2BB | 38 | 13 |
| Ex. 2CC | 38 | 21 |
| Ex. 2DD | 66 | 38 |
| Ex. 2EE | 150 | 46 |
| Ex. 2FF | 94 | 42 |
| Ex. 2GG | 20 | 10 |
| Ex. 2HH | 18 | 10 |
| Ex. 2II | 37 | 12 |
| Ex. 2JJ | 45 | 5 |
| Ex. 2KK | 38 | 12 |
| Ex. 2LL | 649 | 123 |
| Ex. 2MM | 71 | 58 |
| Ex. 3 | 204 | 107 |
| Ex. 4A | 48 | 20 |
| Ex. 4B | 77 | 31 |
| Ex. 4C | 68 | 48 |

-continued

| Compound | Human Plasma DPP-IV (nM) | Rat Plasma DPP-IV (nM) |
|---|---|---|
| Ex. 4D | 104 | 59 |
| Ex. 5 | 5 | 4 |

In view of their ability to inhibit DPP-IV, the compounds of formula I, and their corresponding pharmaceutically acceptable acid addition salts, are useful in treating conditions mediated by DPP-IV inhibition. Based on the above and findings in the literature, it is expected that the compounds disclosed herein are useful in the treatment of conditions such as non-insulin-dependent diabetes mellitus, arthritis, obesity, allograft transplantation and calcitonin-osteoporosis. In addition, based on the roles of glucagon-like peptides (such as GLP-1 and GLP-2) and their association with DPP-IV inhibition, it is expected that the compounds disclosed herein are useful for example, to produce a sedative or anxiolytic effect, or to attenuate post-surgical catabolic changes and hormonal responses to stress, or to reduce mortality and morbidity after myocardial infarction, or in the treatment of conditions related to the above effects which may be mediated by GLP-1 and/or GLP-2 levels.

More specifically, for example, the compounds of formula I, and their corresponding pharmaceutically acceptable acid addition salts, improve early insulin response to an oral glucose challenge and, therefore, are useful in treating non-insulin-dependent diabetes mellitus. The ability of the compounds of formula I, and their corresponding pharmaceutically acceptable acid addition salts, to improve early insulin response to an oral glucose challenge may be measured in insulin resistant rats according to the following method:

Male Sprague-Dawley rats that had been fed a high fat diet (saturated fat=57% calories) for 2–3 weeks were fasted for approximately 2 hours on the day of testing, divided into groups of 7–10, and dosed orally with 10 μmol/kg of test compound in carboxymethylcellulose. Each of the test compounds administered orally at 10 μmol/kg ten minutes prior to the administration of glucose (1 g/kg p.o.), led to a significant inhibition of plasma DPP-IV activity during the study. For example, the compound of Example 2N, administered orally at 10 μmol/kg (n=7–8) ten minutes prior to the administration of glucose (1 g/kg p.o.), led to an 80% inhibition of plasma DPP-IV activity during the study. Blood samples, obtained at various time-points from chronic jugular vein catheters, were analyzed for plasma glucose concentration. Data are expressed as % decrease of the area under the plasma glucose curve compared to vehicle-treated control animals. The following result was obtained:

| Compound | Decrease of Plasma Glucose Excursion at 10 μmol/kg (p = 0.01) |
|---|---|
| Ex. 2N | 39% |

The precise dosage of the compounds of formula I, and their corresponding pharmaceutically acceptable acid addition salts, to be employed for treating conditions mediated by DPP-IV inhibition depends upon several factors, including the host, the nature and the severity of the condition being treated, the mode of administration and the particular compound employed. However, in general, conditions mediated by DPP-IV inhibition are effectively treated when a compound of formula I, or a corresponding pharmaceutically acceptable acid addition salt, is administered enterally, e.g., orally, or parenterally, e.g., intravenously, preferably orally, at a daily dosage of 0.002–5, preferably 0.02–2.5 mg/kg body weight or, for most larger primates, a daily dosage of 0.1–250, preferably 1–100 mg. A typical oral dosage unit is 0.01–0.75 mg/kg, one to three times a day. Usually, a small dose is administered initially and the dosage is gradually increased until the optimal dosage for the host under treatment is determined. The upper limit of dosage is that imposed by side effects and can be determined by trial for the host being treated.

The compounds of formula I, and their corresponding pharmaceutically acceptable acid addition salts, may be combined with one or more pharmaceutically acceptable carriers and, optionally, one or more other conventional pharmaceutical adjuvants and administered enterally, e.g., orally, in the form of tablets, capsules, caplets, etc. or parenterally, e.g., intravenously, in the form of sterile injectable solutions or suspensions. The enteral and parenteral compositions may be prepared by conventional means.

The compounds of formula I, and their corresponding pharmaceutically acceptable acid addition salts, may be formulated into enteral and parenteral pharmaceutical compositions containing an amount of the active substance that is effective for treating conditions mediated by DPP-IV inhibition, such compositions in unit dosage form and such compositions comprising a pharmaceutically acceptable carrier.

The compounds of formula I (including those of each of the subscopes thereof and each of the examples) may be administered in enantiomerically pure form (e.g., ee>98%, preferably>99%) or together with the R enantiomer, e.g., in racemic form. The above dosage ranges are based on the compounds of formula I (excluding the amount of the R enantiomer).

The present invention furthermore refers to a combination, especially a combined preparation or pharmaceutical composition, respectively, comprising a compound of formula I or a pharmaceutically acceptable acid addition salt thereof and at least one different antidiabetic agent (e.g. one or two different antidiabetic agents) or a pharmaceutically acceptable salt thereof.

A suitable antidiabetic agent is e.g. selected from the group consisting of insulin signalling pathway modulators, like inhibitors of protein tyrosine phosphatases (PTPases), non-small molecule mimetic compounds and inhibitors of glutamine-fructose-6-phosphate amidotransferase (GFAT), compounds influencing a dysregulated hepatic glucose production, like inhibitors of glucose-6-phosphatase (G6Pase), inhibitors of fructose-1,6-bisphosphatase (F-1,6-BPase), inhibitors of glycogen phosphorylase (GP), glucagon receptor antagonists and inhibitors of phosphoenolpyruvate carboxykinase (PEPCK), pyruvate dehydrogenase kinase (PDHK) inhibitors, insulin sensitivity enhancers, insulin secretion enhancers, α-glucosidase inhibitors, inhibitors of gastric emptying, insulin, and $\alpha_2$-adrenergic antagonists for simultaneous, separate or sequential use.

Examples of "inhibitors of PTPase" include, but are not limited to those disclosed in U.S. Pat. Nos. 6,057,316, 6,001,867, WO 99/58518, WO 99/58522, WO 99/46268, WO 99/46267, WO 99/46244, WO 99/46237, WO 99/46236, WO 99/15529 and by Poucheret et al in Mol. Cell Biochem. 1998, 188, 73–80.

Examples of "non-small molecule mimetic compounds" include, but are not limited to those disclosed in Science 1999, 284; 974–97, especially L-783,281, and WO 99/58127, especially CLX-901.

Examples of "inhibitors of GFAT" include, but are not limited to those disclosed in Mol. Cell. Endocrinol. 1997, 135(1), 67–77.

The term "inhibitors of G6Pase" used herein means a compound or composition which reduces or inhibits hepatic gluconeogenesis by decreasing or inhibiting the activity of G6Pase. Examples of such compounds are disclosed in WO 00/14090, WO 99/40062, WO 98/40385, EP682024 and Diabetes 1998, 47, 1630–1636.

The term "inhibitors of F-1,6-BPase" used herein means a compound or composition which reduces or inhibits hepatic gluconeogenesis by decreasing or inhibiting the activity of F-1,6-BPase. Examples of such compounds are disclosed in WO 00/14095, WO 99/47549, WO 98/39344, WO 98/39343 and WO 98/39342.

The term "inhibitors of GP" used herein means a compound or composition which reduces or inhibits hepatic glycogenolysis by decreasing or inhibiting the activity of GP. Examples of such compounds are disclosed in EP 978279, U.S. Pat. No. 5,998,463, WO 99/26659, EP 846464, WO 97/31901, WO 96/39384, WO9639385 and in particular CP-91149 as described in Proc. Natl. Acad Sci USA 1998, 95, 1776–1781.

The term "glucagon receptor antagonists" as used herein relates in particular to the compounds described in WO 98/04528, especially BAY27-9955, and those described in Bioorg Med. Chem. Lett 1992, 2, 915–918, especially CP-99,711, J. Med. Chem. 1998, 41, 5150–5157, especially NNC 92-1687, and J. Biol Chem. 1999, 274; 8694–8697, especially L-168,049 and compounds disclosed in U.S. Pat. No. 5,880,139, WO 99/01423, U.S. Pat. No. 5,776,954, WO 98/22109, WO 98/22108, WO 98/21957 and WO 97/16442.

The term "inhibitors of PEPCK" used herein means a compound or composition which reduces or inhibits hepatic gluconeogenesis by decreasing or inhibiting the activity of PEPCK. Examples of such compounds are disclosed in U.S. Pat. No. 6,030,837 and Mol. Biol. Diabetes 1994 2 283–99.

The term "PDHK inhibitors" as used herein means inhibitors of pyruvate dehydrogenase kinase and include, but are not limited to, those compounds disclosed by Aicher et al in J. Med. Chem. 42 (1999) 2741–2746.

The term "insulin sensitivity enhancer" used herein means any and all pharmacological active compounds that enhance the tissue sensitivity towards insulin. Insulin sensitivity enhancers include, e.g., inhibitors of GSK-3, retinoid X receptor (RXR) agonists, agonists of Beta-3 AR, agonists of UCPs, antidiabetic thiazolidinediones (glitazones), non-glitazone type PPARγ agonists, dual PPARγ/PPARα agonists, antidiabetic vanadium containing compounds and biguanides, e.g., metformin.

The insulin sensitivity enhancer is preferably selected from the group consisting of antidiabetic thiazolidinediones, antidiabetic vanadium containing compounds and metformin.

In one preferred embodiment, the insulin sensitivity enhancer is metformin.

Examples of "inhibitors of GSK-3" include, but are not limited to those disclosed in WO 00/21927 and WO 97/41854.

By "RXR agonist" is meant a compound or composition which when combined with RXR homodimers or heterodimers increases the transcriptional regulation activity of RXR, as measured by an assay known to one skilled in the art, including, but not limited to, the "co-transfection" or "cis-trans" assays described or disclosed in U.S. Pat. Nos. 4,981,784, 5,071,773, 5,298,429, 5,506,102, WO89/05355, WO91/06677, WO92/05447, WO93/11235, WO95/18380, PCT/US93/04399, PCT/US94103795 and CA 2,034,220, which are incorporated by reference herein. It includes, but is not limited to, compounds that preferentially activate RXR over RAR (i.e. RXR specific agonists), and compounds that activate both RXR and RAR (i.e. pan agonists). It also includes compounds that activate RXR in a certain cellular context but not others (i.e. partial agonists). Compounds disclosed or described in the following articles, patents and patent applications which have RXR agonist activity are incorporated by reference herein: U.S. Pat. Nos. 5,399,586 and 5,466,861, WO96/05165, PCT/US95/16842, PCT/US95/16695, PCT/US93/10094, WO94/15901, PCT/US92/11214, WO93/11755, PCT/US93/10166, PCT/US93/10204, WO094/15902, PCT/US93/03944, WO93/21146, provisional applications No. 60/004,897 and No. 60/009,884, Boehm, et al. J. Med. Chem. 38(16):3146–3155, 1994, Boehm, et al. J. Med. Chem. 37(18):2930–2941, 1994, Antras et al., J. Biol. Chem. 266:1157–1161 (1991), Salazar-Olivo et al., Biochem. Biophys. Res. Commun. 204:157–263 (1994) and Safanova, Mol. Cell. Endocrin. 104:201–211 (1994). RXR specific agonists include, but are not limited to, LG 100268 (i.e. 2-[1-(3,5,5,8,8-pentamethyl-5,6,7,8-tetrahydro-2-naphthyl)-cyclopropyl]-pyridine-5-carboxylic acid) and LGD 1069 (i.e. 4-[(3,5,5,8,8-pentamethyl-5,6,7,8-tetrahydro-2-naphthyl)-2-carbonyl]-benzoic acid), and analogs, derivatives and pharmaceutically acceptable salts thereof. The structures and syntheses of LG 100268 and LGD 1069 are disclosed in Boehm, et al. J. Med. Chem. 38(16): 3146–3155, 1994, incorporated by reference herein. Pan agonists include, but are not limited to, ALRT 1057 (i.e. 9-cis retinoic acid), and analogs, derivatives and pharmaceutically acceptable salts thereof.

Examples of "agonists of Beta-3 AR" include, but are not limited to CL-316,243 (Lederle Laboratories) and those disclosed in WO 99/29672, WO 98/32753, WO 98/20005, WO 98/09625, WO 97/46556, WO 97/37646 and U.S. Pat. No. 5,705,515.

The term "agonists of UCPs" used herein means agonists of UCP-1, preferably UCP-2 and even more preferably UCP-3. UCPs are disclosed in Vidal-Puig et al., Biochem. Biophys. Res. Commun., Vol. 235(1) pp. 79–82 (1997). Such agonists are a compound or composition which increases the activity of UCPs.

The antidiabetic thiazolidinedione (glitazone) is, for example, (S)-((3,4-dihydro-2-(phenyl-methyl)-2H-1-benzopyran-6-yl)methyl-thiazolidine-2,4-dione (englitazone), 5-{[4-(3-(5-methyl-2-phenyl-4-oxazolyl)-1-oxopropyl)-phenyl]-methyl}-thiazolidine-2,4-dione (darglitazone), 5-{[4-(1-methyl-cyclohexyl)methoxy)-phenyl]methyl}-thiazolidine-2,4-dione (ciglitazone), 5-{[4-(2-(1-indolyl)ethoxy)phenyl]methyl}-thiazolidine-2,4-dione (DRF2189), 5-{4-[2-(5methyl-2phenyl-4-oxazolyl)-ethoxy)]benzyl}-thiazolidine-2,4-dione (BM-13.1246), 5-(2-naphthylsulfonyl)-thiazolidine-2,4-dione (AY-31637), bis{4-[(2,4-dioxo-5-thiazolidinyl)methyl]phenyl}methane (YM268), 5-{4-[2-(5-methyl-2-phenyl-4-oxazolyl)-2-hydroxyethoxy]benzyl}-thiazolidine-2,4-dione (AD-5075), 5-[4-(1-phenyl-1-cyclopropanecarbonylamino)-benzyl]-thiazolidine-2,4-dione (DN-108) 5-{[4-(2-(2,3-dihydroindol-1-yl)ethoxy)phenylmethyl}-thiazolidine-2,4-dione, 5-[3-(4-chloro-phenyl])-2-propynyl]-5-phenylsulfonyl)thiazolidine-2,4-dione, 5-[3-(4-chlorophenyl])-2-propynyl]-5-(4-fluorophenylsulfonyl) thiazolidine-2,4-dione, 5-{[4-(2-(methyl-2-pyridinyl-amino)-ethoxy)phenyl]methyl}thiazolidine-2,4-dione (rosiglitazone), 5-{[4-(2-(5-ethyl-2-pyridyl)ethoxy)phenyl]- methyl}thiazolidine-2,4-dione (pioglitazone), 5-{[4-((3,4-dihydro-6-hydroxy-2,5,7,8-tetramethyl-2H-1-benzopyran-2-yl)methoxy)-phenyl]-methyl}-thiazolidine-2,4-dione (troglitazone), 5-[6-(2-fluoro-benzyloxy)-naphthalen-2-ylmethyl]-thiazolidine-2,4-dione (MCC555), 5-{[2-(2-naphthyl)-benzoxazol-5-yl]-methyl}thiazolidine-2,4-dione (T-174) and 5-(2,4-dioxothiazolidin-5-ylmethyl)-2-methoxy-N-(4-trifluoromethyl-benzyl)benzamide (KRP297).

The glitazones 5-{[4-(2-(5-ethyl-2-pyridyl)ethoxy)phenyl]-methyl}thiazolidine-2,4-dione (pioglitazone, EP 0 193 256 A1), 5-{[4-(2-(methyl-2-pyridinyl-amino)-ethoxy)phenyl]methyl}-thiazolidine-2,4-dione (rosiglitazone, EP 0 306 228 A1), 5-{[4-((3,4-dihydro-6-hydroxy-2,5,7,8-tetramethyl-2H-1-benzopyran-2-yl)methoxy)-phenyl]-methyl}thiazolidine-2,4-dione (troglitazone, EP 0 139 421), (S)-((3,4-dihydro-2-(phenyl-methyl)-2H-1-benzopyran-6-yl)methyl-thiazolidine-2,4-dione (englitazone, EP 0 207 605 B1), 5-(2,4-dioxothiazolidin-5-ylmethyl)-2-methoxy-N-(4-trifluoromethyl-benzyl)benzamide (KRP297, JP 10087641-A), 5-[6-(2-fluoro-benzyloxy)naphthalen-2-ylmethyl]thiazolidine-2,4-dione (MCC555, EP 0 604 983 B1), 5-{[4-(3-(5-methyl-2-phenyl-4-oxazolyl)-1-oxopropyl)-phenyl]-methyl}-thiazolidine-2,4-dione (darglitazone, EP 0 332 332), 5-(2-naphthylsulfonyl)-thiazolidine-2,4-dione (AY-31637, U.S. Pat. No. 4,997,948), 5-{[4-(1-methyl-cyclohexyl)methoxy)-phenyl]methyl}-thiazolidine-2,4-dione (ciglitazone, U.S. Pat. No. 4,287,200) are in each case generically and specifically disclosed in the documents cited in brackets beyond each substance, in each case in particular in the compound claims and the final products of the working examples, the subject-matter of the final products, the pharmaceutical preparations and the claims are hereby incorporated into the present application by reference to these publications. The preparation of DRF2189 and of 5-{[4-(2-(2,3-dihydroindol-1-yl)ethoxy)phenyl]methyl}-thiazolidine-2,4-dione is described in B. B. Lohray et al., J. Med. Chem. 1998, 41, 1619–1630; Examples 2d and 3g on pages 1627 and 1628. The preparation of 5-[3-(4-chlorophenyl])-2-propynyl]-5-phenylsulfonyl)-thiazolidine-2,4-dione and the other compounds in which A is phenylethynyl mentioned herein can be carried out according to the methods described in J. Wrobel et al., J. Med. Chem. 1998, 41,1084–1091.

In particular, MCC555 can be formulated as disclosed on page 49, lines 30 to 45, of EP 0 604 983 B1; englitazone as disclosed from page 6, line 52, to page 7, line 6, or analogous to Examples 27 or 28 on page 24 of EP 0 207 605 B1; and darglitazone and 5-{4-[2-(5-methyl-2-phenyl-4-oxazolyl)-ethoxy)]benzyl}-thiazolidine-2,4-dione (BM-13.1246) can be formulated as disclosed on page 8, line 42 to line 54 of EP 0 332 332 B1. AY-31637 can be administered as disclosed in column 4, lines 32 to 51 of U.S. Pat. No. 4,997,948 and rosiglitazone as disclosed on page 9, lines 32 to 40 of EP 0 306 228 A1, the latter preferably as its maleate salt. Rosiglitazone can be administered in the form as it is marketed e.g. under the trademark AVANDIA™. Troglitazone can be administered in the form as it is marketed e.g. under the trademarks ReZulinr™, PRELAY™, ROMOZIN™ (in the United Kingdom) or NOSCAL™ (in Japan). Pioglitazone can be administered as disclosed in Example 2 of EP 0 193 256 A1, preferably in the form of the monohydrochloride salt. Corresponding to the needs of the single patient it can be possible to administer pioglitazone in the form as it is marketed e.g. under the trademark ACTOS™. Ciglitazone can, for example, be formulated as disclosed in Example 13 of U.S. Pat. No. 4,287,200.

Non-glitazone type PPARγ agonists are especially N-(2-benzoylphenyl)-L-tyrosine analogues, e.g. GI-262570, and JTT501.

The term "dual PPARγ/PPARα agonists" as used herein means compounds which are at the same time PPARγ and PPARα agonists. Preferred dual PPARγ/PPARα agonists are especially those ω-[(oxoquinazolinylalkoxy)phenyl]alkanoates and analogs thereof, very especially the compound DRF-554158, described in WO 99/08501 and the compound NC-2100 described by Fukui in Diabetes 2000, 49(5), 759–767.

Preferably, the antidiabetic vanadium containing compound is a physiologically tolerable vanadium complex of a bidentate monoprotic chelant, wherein said chelant is an a-hydroxypyrone or α-hydroxypyridinone, especially those disclosed in the Examples of U.S. Pat. No. 5,866,563, of which the working examples are hereby incorporated by reference, or a pharmaceutically acceptable salt thereof.

The preparation of metformin (dimethyldiguanide) and its hydrochloride salt is state of the art and was disclosed first by Emil A. Werner and James Bell, J. Chem. Soc. 121, 1922, 1790–1794. Metformin, can be administered e.g. in the form as marketed under the trademarks GLUCOPHAGE™.

Insulin secretion enhancers are pharmacological active compounds having the property to promote secretion of insulin from pancreatic β cells. Examples for insulin secretion enhancers include glucagon receptor antagonists (see above), sulphonyl urea derivatives, incretin hormones, especially glucagon-like peptide-1 (GLP-1) or GLP-1 agonists, β-cell imidazoline receptor antagonists, and short-acting insulin secretagogues, like antidiabetic phenylacetic acid derivatives, antidiabetic D-phenylalanine derivatives and BTS 67582 described by T. Page et al in Br. J. Pharmacol. 1997, 122, 1464–1468.

The sulphonyl urea derivative is, for example, glisoxepid, glyburide, glibenclamide, acetohexamide, chloropropamide, glibornuride, tolbutamide, tolazamide, glipizide, carbutamide, gliquidone, glyhexamide, phenbutamide or tolcyclamide; and preferably glimepiride or gliclazide. Tolbutamide, glibenclamide, gliclazide, glibornuride, gliquidone, glisoxepid and glimepiride can be administered e.g. in the form as they are marketed under the trademarks RASTINON HOECHST™, AZUGLUCON™, DIAMICRON™, GLUBORID™, GLURENORM™, PRO-DIABAN™ and AMARYL™, respectively.

GLP-1 is a insulinotropic proteine which was described, e.g., by W. E. Schmidt et al. in Diabetologia 28, 1985, 704–707 and in U.S. Pat. No. 5,705,483. The term "GLP-1 agonists" used herein means variants and analogs of GLP-1(7-36)NH$_2$ which are disclosed in particular in U.S. Pat. Nos. 5,120,712, 5,118,666, 5,512,549, WO 91/11457 and by C. Orskov et al in J. Biol. Chem. 264 (1989) 12826. The term "GLP-1 agonists" comprises especially compounds like GLP-1(7-37), in which compound the carboxy-terminal amide functionality of Arg[36] is displaced with Gly at the 37$^{th}$ position of the GLP-1(7-36)NH$_2$ molecule and variants and analogs thereof including GLN$^9$-GLP-1(7-37), D-GLN$^9$-GLP-1(7-37), acetyl LYS$^9$-GLP-1(7-37), LYS$^{18}$-GLP-1(7-37) and, in particular, GLP-1(7-37)OH, VAL$^8$-GLP-1(7-37), GLY$^8$-GLP-1(7-37), THR$^8$-GLP-1(7-37) imidazopropionyl-GLP-1. Special preference is also given to the GLP agonist analog exendin-4, described by Greig et al in Diabetologia 1999, 42, 45–50.

The term "β-cell imidazoline receptor antagonists" as used herein means compounds as those described in WO 00/78726 and by Wang et al in J. Pharmacol. Exp. Ther. 1996; 278; 82–89, e.g. PMS 812.

The antidiabetic phenylacetic acid derivative is preferably repaglinide or a pharmaceutically acceptable salt thereof.

Most preferably, the antidiabetic D-phenylalanine derivative is nateglinide or a pharmaceutically acceptable salt thereof.

Nateglinide (N-[(trans-4-isopropylcyclohexyl)-carbonyl]-D-phenylalanine, EP 196222 and EP 526171) and repaglinide ((S)-2-ethoxy-4-{2-[[3-methyl-1-[2-(1-piperidinyl)phenyl]butyl]amino]-2-oxoethyl}benzoic acid, EP 0 147 850 A2, in particular Example 11 on page 61, and EP 0 207 331 A1) are in each case generically and specifically disclosed in the documents cited in brackets beyond each substance, in each case in particular in the compound claims and the final products of the working examples, the subject-matter of the final products, the pharmaceutical preparations and the claims are hereby incorporated into the present application by reference to these publications. The term nateglinide as used herein comprises crystal modifications (polymorphs) such as those disclosed in EP 0526171 B1 or U.S. Pat. No. 5,488,510, respectively, the subject matter of which is incorporated by reference to this application, especially the subject matter of claims 8 to 10 as well as the corresponding references to the B-type crystal modification. Preferably, in the present invention the B- or H-type, more preferably the H-type, is used. Repaglinde can be administered in the form as it is marketed e.g. under the trademark NovoNorm™. Nateglinide can be administered in the form as it is marketed e.g. under the trademark STARLIX™.

α-Glucosidase inhibitors are pharmacological active compounds which inhibit small intestinal □-glucosidase enzymes which break down non-adsorbable complex carbohydrates into absorbable monosaccharides. Examples for such compounds are acarbose, N-(1,3-dihydroxy-2-propyl) valiolamine (voglibose) and the 1-deoxynojirimycin derivative miglitol. Acarbose is 4",6"-dideoxy-4"-[(1S)-(1,4,6/5)-4,5,6-trihydroxy-3-hydroxymethyl-2-cyclo-hexenylaminolmaltotriose. The structure of acarbose can as well be described as O-4,6-dideoxy-4-{[1S,4R,5S,6S]-4,5,6-trihydroxy-3-(hydroxymethyl)-2-cyclohexen-1-yl]-amino}-α-D-glucopyranosyl-(1→4)-O-α-D-glucopyranosyl-(1→4)-D-glucopyranose. Acarbose (U.S. Pat. No. 4,062,950 and EP 0 226 121), is generically and specifically disclosed in the documents cited in brackets, in particular in the compound claims and the final products of the working examples, the subject-matter of the final products, the pharmaceutical preparations and the claims are hereby incorporated into the present application by reference to these publications. Corresponding to the needs of the single patient it can be possible to administer acarbose in the form as it is marketed e.g. under the trademark GLUCOBAY™. Miglitol can be administered in the form as it is marketed e.g. under the trademark DIASTABOL 50™.

The □-glucosidase inhibitor is preferably selected from the group consisting of acarbose, voglibose and miglitol.

Examples of "inhibitors of gastric emptying" other than GLP-1 include, but are not limited to those disclosed in J. Clin. Endocrinol. Metab. 2000, 85(3), 1043–1048, especially CCK-8, and in Diabetes Care 1998; 21; 897–893, especially Amylin and analogs thereof, e.g. Pramlintide. Amylin is also described e.g. by O. G. Kolterman et al. in Diabetologia 39, 1996, 492–499.

Examples of "$\alpha_2$-adrenergic antagonists" include, but are not limited to midaglizole described in Diabetes 36, 1987, 216–220.

Comprised are likewise the corresponding stereoisomers as well as the corresponding polymorphs, e.g. crystal modifications, which are disclosed in the cited patent documents.

In a very preferred embodiment of the invention, the further antidiabetic compound is selected from the group consisting of nateglinide, repaglinide, metformin, rosiglitazone, pioglitazone, troglitazone, glisoxepid, glyburide, glibenclamide, acetohexamide, chloropropamide, glibomuride, tolbutamide, tolazamide, glipizide, carbutamide, gliquidone, glyhexamide, phenbutamide, tolcyclamide, glimepiride and gliclazide, or the pharmaceutically acceptable salt of such a compound. Most preferred is nateglinide, repaglinide or metformin, respectively, furthermore, pioglitazone, rosiglitazone or troglitazone respectively.

The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference. Any person skilled in the art is fully enabled to identify the active agents and, based on these references, likewise enabled to manufacture and test the pharmaceutical indications and properties in standard test models, both in vitro and in vivo.

The combinations according to the present invention can used especially in the prevention, delay of progression or treatment of conditions mediated by dipeptidylpeptidase-IV (DPP-IV), in particular diabetes, more particular type 2 diabetes mellitus, conditions of impaired glucose tolerance (IGT), conditions of impaired fasting plasma glucose, metabolic acidosis, ketosis, arthritis, obesity and osteoporosis; for the prevention, delay of progression or treatment of such conditions; the use of such combination for the cosmetic treatment of a mammal in order to effect a cosmetically beneficial loss of body weight.

The person skilled in the pertinent art is fully enabled to select a relevant animal test model to prove the hereinbefore and hereinafter indicated therapeutic indications and beneficial effects.

The invention furthermore relates to a commercial package comprising a compound according to the present invention or a combination according to the present invention together with instructions for simultaneous, separate or sequential use The following examples show representative compounds encompassed by this invention and their synthesis. However, it should be clearly understood that they are for purposes of illustration only.

EXAMPLE 1

1-[[[2-[(5-chloro-2-pyridinyl)amino]-1,1-dimethylethyl]amino]acetyl]-2-cyano-(S)-pyrrolidine, monohydrochloride A. 1-Chloroacetyl-2-(S)-cyanopyrrolidine To a mechanically stirred solution of 20.0 g (180.0 mmol) of chloroacetylchloride and 97 g (0.70 mmol) of potassium carbonate in 150 mL of tetrahydrofuran is added a solution of L-prolinamide 20.0 g (180.0 mmol) in 500 mL of tetrahydrofuran in a dropwise fashion over 45 minutes. This reaction is then mechanically stirred for an additional two hours at room temperature. The reaction is then filtered to remove potassium salts and the filtrate is dried over $Na_2SO_4$. The $Na_2SO_4$ is then removed via filtration and to this colorless filtrate is added trifluoroacetic anhydride (25.0 mL, 0.180 mmol) in one portion. The reaction is then magnetically stirred for 1 hour at room temperature and the resulting clear yellow/orange solution is concentrated via rotovap. The excess trifluoroacetic anhydride is removed by adding ethyl acetate to the concentrated oil and reconcentrating via rotovap. This removing operation is performed three times.

The resulting oil is partitioned between ethyl acetate and water. The product is then extracted into the ethyl acetate and the aqueous layer is then washed twice with ethyl acetate. The combined organic layers are then washed successively with water and brine dried over magnesium sulfate, filtered and concentrated to obtain 1-chloroacetyl-2-(S)-cyanopyrrolidine as a yellow solid.

Alternatively, the reaction may be carried out by using, as base, a mixture, e.g. 2-ethyl-hexanoic acid/sodium hydride.

B. Preparation of the Title Compound in Free Base Form

To a 200 ml flask containing 60 ml of $CH_2Cl_2$ is added 1.85 g (9.27 mmol) of 2-[(5-chloro-2-pyrindinyl)amino]-1,1-dimethylethylamine and 3.95 g of $K_2CO_3$ and the mixture is cooled in an ice bath. To this cooled mixture is slowly added 1.20 g (7.14 mmol) of the above chloride compound prepared in A) dissolved in 30 ml of $CH_2Cl_2$. The resultant mixture is stirred at room temperature for 2 days. The $K_2CO_3$ is then removed via filtration and the filtrate is concentrated via rotovaping. The crude form is then purified on silica gel employing a SIMS/Biotage Flash chromatography system and a 3% solution of methanol in methylene chloride as the eluent to yield the title compound in free base form as a sticky yellow solid.

C. Preparation of the Title Compound

After dissolving the free base compound prepared in B) above in 20 ml of dry tetrahydrofuran, hydrogen chloride gas is bubbled into the solution for 20 seconds. The reaction was stirred for five minutes and then concentrated via rotovap and then high vacuum pumping to obtain the title compound as an off-white solid, m.p. 164°–166° C. $^{13}C$ NMR (ppm)=119.17.

EXAMPLE 2

Following essentially the procedure of Example 1, and using in place of the amine therein an equivalent amount of the above described or commercially available:

a) 1-[2-[(5-cyano-2-pyridinyl)amino]-1,1-dimethylethyl]amine;
b) 1-[2-[(5-trifluoromethyl-2-pyridinyl)amino]-1,1-dimethylethyl]amine;
c) 1-[2-[(4-methylbenzoyl)amino]-1,1-dimethylethyl]amine;
d) 1-[2-[(3-chloro-2-pyridinyl)amino]-1,1-dimethylethyl]amine;
e) 1-[2-[(4-trifluoromethyl-2-pyridinyl)amino]-1,1-dimethylethyl]amine;
f) 1-[2-[(3,5-dichloro-2-pyridinyl)amino]-1,1-dimethylethyl]amine;
g) 1-[2-[(3-trifluoromethyl-2-pyridinyl)amino]-1,1-dimethylethyl]amine;
h) 1-[2-[(2,2-dimethyl-1-oxopropyl)amino]-1,1-dimethylethyl]amine;
i) 1-[2-[(4-chlorobenzoyl)amino]-1,1-dimethylethyl]amine;
j) 1-[2-[(diisopropylamino)carbonyl]amino]-1,1-dimethylethyl]amine;
k) 1-[2-[(4-chlorophenyl)amino]carbonyl]amino]-1,1-dimethylethyl]amine;
l) 1-[4-[(5-cyano-2-pyridinyl)amino]cyclohexyl]amine;
m) 1-[4-[(phenylsulfonyl)amino]cyclohexyl]amine;
n) 1-[4-(benzoylamino)cyclohexyl]amine;
o) 1-[4-[[(4-trifluoromethyl)-2-pyrimidinyl]amino]cyclohexyl]amine;
p) 1-[4-[(3-trifluoromethyl-2-pyridinyl)amino]cyclohexyl]amine;
q) 1-[[4-[(4-chlorophenyl)sulfonyl]amino]cyclohexyl]amine;
r) 1-[4-[(5-trifluoromethyl-2-pyridinyl)amino]cyclohexyl]amine;
s) 1-[4-[(2-chloro-4-pyrimidinyl)amino]cyclohexyl]amine;
t) 1-[4-[(4-chlorobenzoyl)amino]cyclohexyl]amine;
u) 1-[4-[(2,2-dimethyl-1-oxopropyl)amino]cyclohexyl]amine;
v) 1-[4-[(2-benzothiazolyl)amino]cyclohexyl]amine;
w) 1-[4-[(4-cyanophenyl)amino]cyclohexyl]amine;
x) 1-[4-[(cyclohexylcarbonyl)amino]cyclohexyl]amine;
y) 1-[4-[(5-chloro-2-benzothiazolyl)amino]cyclohexyl]amine;
z) 1-[4-[[[(4-trifluoromethyl)phenyl]sulfonyl]amino]cyclohexyl]amine;
aa) 1-[4-[[(2-thienyl)sulfonyl]amino]cyclohexyl]amine;
bb) 1-[2-(4-fluorophenyl)-1,1-dimethylethyl]amine (commercially available);
cc) 1-(1,1-dimethyl-2-phenylethyl)amine (commercially available);
dd) 1-(4-pentylbicyclo[2.2.2]oct-1-yl)amine (commercially available);
ee) 1-[4-[4-(trifluoromethyl)phenoxy]cyclohexyl]amine;
ff) 1-[[4-[4-(chlorophenoxy)]cyclohexyl]amine;
gg) 1-[4-[(3-trifluoromethyl)phenoxy]cyclohexyl]amine;
hh) 1-[4-(3-chlorophenoxy)cyclohexyl]amine;
ii) 1-[1-[[(4-chlorophenyl)amino]carbonyl]-4-piperidinyl]amine;
jj) 1-[1-[(diisopropylamino)carbonyl]-4-piperidinyl]amine;
kk) 1-[1-(4-phenyl-2-thiazolyl) 4-piperdinyl]amine;
ll) 1-[1-[4-(4-chlorophenyl)-2-thiazolyl]-4-piperidinyl]amine; and
mm) 1-[1-[4-(4-methoxyphenyl)-2-thiazolyl]-4-piperidinyl]amine, there is obtained the following products as hydrochloride salt or, if (C) in Example 1 is not performed, the free base:

A) 1-[[[2-[(5-cyano-2-pyridinyl)amino]-1,1-dimethylethyl]amino]acetyl]-2-cyano-(S)-pyrrolidine, free base as a white solid (melting point=47°–49° C., $^{13}C$ NMR δ118.87 ppm (CN));

B) 1-[[[2-[(5-trifluoromethyl-2-pyridinyl)amino]-1,1-dimethylethyl]amino]acetyl]-2-cyano-(S)-pyrrolidine, dihydrochloride as an off-white solid (melting point=170°–172° C., $^{13}C$ NMR δ119.31 ppm (CN));

C) 1-[[[2-[(4-methylbenzoyl)amino]-1,1-dimethylethyl]amino]acetyl]-2-cyano-(S)pyrrolidine, free base as a white solid (melting point=40°–42° C., $^{13}C$ NMR δ118.11 ppm (CN));

D) 1-[[[2-[(3-chloro-2-pyridinyl)amino]-1,1-dimethylethyl]amino]acetyl]-2-cyano-(S)-pyrrolidine, dihydrochloride as an off-white solid (melting point=144°–146° C., $^{13}C$ NMR δ118.21 ppm (CN));

E) 1-[[[2-[(4-trifluoromethyl-2-pyridinyl)amino]-1,1-dimethylethyl]amino]acetyl]-2-cyano-(S)-pyrrolidine, free base as a white solid (melting point=38°–40° C., $^{13}C$ NMR δ119.57 ppm (CN));

F) 1-[[[2-[(3,5-dichloro-2-pyridinyl)amino]-1,1-dimethylethyl]amino]acetyl]-2-cyano-(S)-pyrrolidine, dihydrochloride as a white solid (melting point=108°–110° C., $^{13}C$ NMR δ119.34 ppm (CN));

G) 1-[[[2-[(3-trifluoromethyl-2-pyridinyl)amino]-1,1-dimethylethyl]amino]acetyl]-2-cyano-(S)-pyrrolidine, dihydrochloride as an off-white solid (melting point=112°–114° C., $^{13}C$ NMR δ118.18 ppm (CN));

H) 1-[[[2-[(2,2-dimethyl-1-oxopropyl)amino]-1,1-dimethylethyl]amino]acetyl]-2-cyano-(S)-pyrrolidine, monohydrochloride as a white solid (melting point=225°–227° C., $^{13}C$ NMR δ119.24 ppm (CN));

I) 1-[[[2-[(4-chlorobenzoyl)amino]-1,1-dimethylethyl]amino]acetyl]-2-cyano-(S)-pyrrolidine, monohydrochloride as a white crystalline solid (melting point=121°–123° C., $^{13}C$ NMR δ119.34 ppm (CN));

J) 1-[[[2-[[(diisopropylamino)carbonyl]amino]-1,1-dimethylethyl]amino]acetyl]-2-cyano-(S)-pyrrolidine, monohydrochloride as an orange solid (melting point=128°–130° C., $^{13}$C NMR δ118.10 ppm (CN));

K) 1-[[[2-[[[(4-chlorophenyl)amino]carbonyl]amino]-1,1-dimethylethyl]amino]acetyl]-2-cyano-(S)-pyrrolidine, monohydrochloride as a yellow solid (melting point=112°–114° C., $^{13}$C NMR δ119.67 ppm (CN));

L) 1-[[[4-[(5-cyano-2-pyridinyl)amino]cyclohexyl]amino]acetyl]-2-cyano-(S)-pyrrolidine, dihydrochloride as a white solid (melting point=242°–244° C., $^{13}$C NMR δ119.31 ppm (CN));

M) 1-[[[4-[(phenylsulfonyl)amino]cyclohexyl]amino]acetyl]-2-cyano-(S)-pyrrolidine, monohydrochloride as a white solid (melting point=120°–122° C., $^{13}$C NMR δ119.25 ppm (CN));

N) 1-[[[4-(benzoylamino)cyclohexyl]amino]acetyl]-2-cyano-(S)-pyrrolidine, free base as a white fluffy solid (melting point=78°–80°, $^{13}$C NMR δ119.68 ppm (CN));

O) 1-[[[4-[[(4-trifluoromethyl)-2-pyrimidinyl]amino]cyclohexyl]amino]acetyl]-2-cyano-(S)-pyrrolidine, dihydrochloride as a white solid (decomposed >300° C., $^{13}$C NMR δ119.97 ppm (CN));

P) 1-[[4-[[(3-trifluoromethyl-2-pyridinyl)amino]cyclohexyl]amino]acetyl]-2-cyano-(S)-pyrrolidine, dihydrochloride as an off-white solid (melting point=289°–292° C., $^{13}$C NMR δ119.65 ppm (CN));

Q) 1-[[[4-[(4-chlorophenyl)sulfonyl]amino]cyclohexyl]amino]acetyl]-2-cyano-(S)-pyrrolidine, monohydrochloride as a white solid (melting point=160°–162° C., $^{13}$C NMR δ119.19 ppm (CN));

R) 1-[[[4-[(5-trifluoromethyl-2-pyridinyl)amino]cyclohexyl]amino]acetyl]-2-cyano-(S)-pyrrolidine, dihydrochloride as a light yellow solid (melting point=270°–273° C., $^{13}$C NMR δ119.02 ppm (CN));

S) 1-[[[4-[(2-chloro-4-pyrimidinyl)amino]cyclohexyl]amino]acetyl]-2-cyano-(S)-pyrrolidine, dihydrochloride as a white solid (melting point=290°–293° C., $^{13}$C NMR δ119.28 ppm (CN));

T) 1-[[[4-[(4-chlorobenzoyl)amino]cyclohexyl]amino]acetyl]-2-cyano-, (S)-pyrrolidine, monohydrochloride as a white solid (melting point=260°–263° C., $^{13}$C NMR δ119.29 ppm (CN));

U) 1-[[[4-[(2,2-dimethyl-1-oxopropyl)amino]cyclohexyl]amino]acetyl]-2-cyano-(S)-pyrrolidine, monohydrochloride as a white solid (melting point=290°–294° C., $^{13}$C NMR δ119.3 ppm (CN));

V) 1-[[[4-[(2-benzothiazolyl)amino]cyclohexyl]amino]acetyl]-2-cyano-(S)-pyrrolidine, dihydrochloride as an off-white solid (melting point=246°–248° C., $^{13}$C NMR δ119.32 ppm (CN));

W) 1-[[[4-[(4-cyanophenyl)amino]cyclohexyl]amino]acetyl]-2-cyano-(S)-pyrrolidine, dihydrochloride as a white solid (melting point=165°–167° C., $^{13}$C NMR δ119.29 ppm (CN));

X) 1-[[[4-[(cyclohexylcarbonyl)amino]cyclohexyl]amino]acetyl]-2-cyano-(S)-pyrrolidine monohydrochloride as a white solid (melting point=189°–190° C., $^{13}$C NMR δ119.34 ppm (CN));

Y) 1-[[[4-[(5-chloro-2-benzothiazolyl)amino]cyclohexyl]amino]acetyl]-2-cyano-(S)-pyrrolidine, dihydrochloride as a white fluffy solid (melting point=290°–294° C., $^{13}$C NMR δ120.32 ppm (CN));

Z) 1-[[[4-[[[(4-trifluoromethyl)phenyl]sulfonyl]amino]cyclohexyl]amino]acetyl]-2-cyano-(S)-pyrrolidine, monohydrochloride as a very light yellow solid (melting point=135°–137° C., $^{13}$C NMR δ119.17 ppm (CN));

AA) 1-[[[4-[(2-thienyl)sulfonyl]amino]cyclohexyl]amino]acetyl]-2-cyano-(S)-pyrrolidine, monohydrochloride as a white fluffy solid (melting point=75°–77° C., $^{13}$C NMR δ119.58 ppm (CN));

BB) 1-[[[2-[(4-fluorophenyl)-1,1-dimethylethyl]amino]acetyl]-2-cyano-(S)-pyrrolidine, monohydrochloride as a light fluffy yellow solid (melting point=198°–200° C., $^{13}$C NMR δ119.28 ppm (CN));

CC) 1-[[(1,1-dimethyl-2-phenylethyl)amino]acetyl]-2-cyano-(S)-pyrrolidine, monohydrochloride as a white solid (melting point=212°–214° C., $^{13}$C NMR δ118.61 ppm (CN));

DD) 1-[[(4-pentylbicyclo[2.2.2]oct-1-yl)amino]acetyl]-2-cyano-(S)-pyrrolidine, monohydrochloride as a fluffy, very light-yellow solid (melting point=99°–102° C., $^{13}$C NMR δ119.25 ppm (CN));

EE) 1-[[[4-[4-(trifluoromethyl)phenoxy]cyclohexyl]amino]acetyl]-2-cyano-(S)-pyrrolidine, monohydrochloride as an off-white solid (decomposed>260° C., $^{13}$C NMR δ119.29 ppm (CN));

FF) 1-[[4-[4-chlorophenoxy)cyclohexyl]amino]acetyl]-2-cyano-(S)-pyrrolidine, monohydrochloride as an off-white solid (melting point=232°–235° C., $^{13}$C NMR δ119.61 ppm (CN));

GG) 1-[[[4-[(3-trifluoromethyl)phenoxy]cyclohexyl]amino]acetyl]-2-cyano-(S)-pyrrolidine, monohydrochloride as a fluffy, very light-yellow solid (melting point=120°–122° C., $^{13}$C NMR δ119.23 ppm (CN));

HH) 1-[[[4-[(3-chlorophenoxy)cyclohexyl]amino]acetyl]-2-cyano-(S)-pyrrolidine, monohydrochloride as a fluffy, light-yellow solid (melting point=72°–74° C., $^{13}$C NMR δ122.02 ppm (CN));

II) 1-[[[1-[[(4-chlorophenyl)amino]carbonyl]-4-piperidinyl]amino]acetyl]-2-cyano-(S)-pyrrolidine, monohydrochloride as a brown solid (melting point=172°–174° C., $^{13}$C NMR δ119.64 ppm (CN));

JJ) 1-[[[1-[(diisopropylamino)carbonyl]-4-piperidinyl]amino]acetyl]-2-cyano-(S)-pyrrolidine, monohydrochloride as a white solid (melting point=82°–84° C., 130 NMR δ118.11 ppm (CN));

KK) 1-[[[1-(4-phenyl-2-thiazolyl)-4-piperidinyl]amino]acetyl]-2-cyano-(S)-pyrrolidine, monohydorchloride as a white solid (melting point=141°–143° C., $^{13}$C NMR δ119.64 ppm (CN));

LL) 1-[[[1-[4-(4-chlorophenyl-2-thiazolyl]-4-piperidinyl]amino]acetyl]-2-cyano-(S)-pyrrolidine, monohydrochloride as an off-white solid (melting point=160°–162° C., $^{13}$C NMR δ119.3 ppm (CN)); and MM) 1-[[[1-[(4-(4-methoxyphenyl)-2-thiazolyl]-4-piperidinyl]amino]acetyl]-2-cyano-(S)-pyrrolidine, monohydrochloride as an off-white solid (melting point=154°–156° C., $^{13}$C NMR δ119.3 ppm (CN)).

EXAMPLE 3

1-[[[1-[(4-chlorophenyl)sulfonyl]-4-piperidinyl]amino]acetyl]-2-cyano-(S)-pyrrolidine, monohydrochloride A. Preparation of the Title Compound as Free Base To a 200 ml flask containing 75 ml of $CH_2Cl_2$ is added 4.0 g (20.0 mmol) of 1-(tert-butoxycarbonylamino)piperidine and 7.4 g (53.3 mmol) of $K_2CO_3$ and the mixture is cooled in an ice bath. To this cooled mixture is slowly added 2.30 g (13.3 mmol) of the above chloride compound prepared in 1A) dissolved in 30 ml of $CH_2Cl_2$. The resultant mixture is stirred at room temperature for 3 days. The $K_2CO_3$ is then removed via filtration and the filtrate is concentrated via rotovaping. The crude form is then purified on silica gel employing a SIMS/Biotage Flash chromatography system and a 3% solution of methanol in methylene chloride as the eluent to yield the intermediate 1-[[[1-[tert-butoxycarbonylamino]-4-piperidinyl]amino]acetyl]-2-cyano-(S)-pyrrolidine in free base form as a golden oil. Deprotection of this t-boc amine with 4.0 M HCl in dioxane at room temperature for 5 hours yielded the dihydrochloride salt of 1-[[[4-piperidinyl]amino]acetyl]-2-cyano-(S)-pyrrolidine as a white solid. To an ice-cold mixture of this amine (300 mg, 0.97 mmol), 30 ml of $CH_2Cl_2$ and 560 mg (4.02 mmol) of $K_2CO_3$ was slowly added 170 mg (0.81 mmol) of 4-chlorobenzenesulfonyl chloride dissolved in 15 ml $CH_2Cl_2$. The resulting mixture was stirred at ice-cold temperature for 2 hours and then at room temperature for 18 hours. Following an EtOAc/water workup, the crude form is then purified on silica gel employing a SIMS/Biotage Flash chromatograhy system and a 3% solution of methanol in methylene chloride as the eluent to yield the title compound in free base form.

B. Preparation of the Title Compound

After dissolving the free base compound prepared above in 15 ml 4.0 M HCl in dioxane, the reaction was stirred at room temperature for 5 hours and then concentrated via a rotovap and then a high vacuum pump to obtain the title compound as a light green solid, m.p. 252°–255° C. $^{13}C$ NMR (ppm)=119.25.

EXAMPLE 4

Following essentially the procedure of Example 3, and using in place of the 4-chlorobenzenesulfonyl chloride therein, an equivalent amount of:
a) cyclohexanecarbonyl chloride;
b) 4-chlorobenzoyl chloride;
c) 4-(trifluoromethyl)phenylsulfonyl chloride; and
d) phenylsulfonyl chloride;
there is obtained:
A) 1-[[[1-(cyclohexylcarbonyl)-4-piperidinyl]amino]acetyl]-2-cyano-(S)-pyrrolidine, monohydrochloride as a white solid (melting point >300° C., $^{13}C$ NMR δ119.61 ppm (CN));
B) 1-[[[1-(4-chlorobenzoyl)-4-piperidinyl]amino]acetyl]-2-[cyano-(S)-pyrrolidine, monohydrochloride as a white solid (melting point=152°–155° C., $^{13}C$ NMR δ119.28 ppm (CN));
C) 1-[[[1-(4-trifluoromethyl)phenyl]sulfonyl]-4-piperidinyl]amino]acetyl]-2-cyano-(S)-pyrrolidine, monohydrochloride as a white solid (melting point >300° C., $^{13}C$ NMR δ119.25 ppm (CN)); and
D) 1-[[(1-phenylsulfonyl-4-piperidinyl)amino]acetyl]-2-cyano-(S)-pyrrolidine, monohydrochloride as a white solid (melting point >300° C., $^{13}C$ NMR δ119.58 ppm (CN)).

EXAMPLE 5

1-[[[4-[(4-Fluorobenzoyl)amino]cyclohexyl]amino] acetyl]-2-cyano-, S)-pyrrolidine, monohydrochloride Preparation of the Title Compound in Free Base Form To a 100 ml flask containing 30 ml of THF is added 0.325 g (1.38 mmol) of 1-[4-[(4-fluorobenzoyl)amino]cyclohexyl] amine and 0.285 g of $K_2CO_3$ and the mixture is cooled in an ice bath. To this cooled mixture is slowly added 0.120 g (0.69 mmol) of 1-chloroacetyl-2-(S)-cyanopyrrolidine in 10 ml of THF. The resultant mixture is stirred at room temperature for 5 days. The potassium salts are then removed via filtration and the filtrate is concentrated via rotovaping. The crude form is then purified on silica gel employing a SIMS/Biotage Flash chromatography system with a 5% solution of methanol in methylene chloride as the eluent to yield the title compound in free base form as white solid.

Preparation of the Title Compound

After dissolving the free base compound prepared above in 20 ml of dry ethyl acetate, hydrogen chloride gas is bubbled into the solution for 20 seconds. The reaction is stirred for 15 min and then concentrated via rotovap, washed twice with 10 ml of anhydrous diethyl ether and dried under high vacuum pumping to obtain the title compound as white solid, m.p. 212°–214° C., $^{13}C$ NMR 119.29 ppm (CN)).

The starting material can be prepared e.g. as follows:

Synthesis of nucleophile: 1-[4-[(4-fluorobenzoyl)amino] cyclohexyl]amine

To an ice-cold solution of trans-1,4-diaminocyclohexane (4.32 g, 37.9 mmol) and $K_2CO_3$ (7.0 g, 50.5 mmol) in 75 ml of $CH_2Cl_2$ is added a solution of benzoyl chloride (1.5 ml, 12.6 mmol) in 25 ml of $CH_2Cl_2$ over 10 minutes. The resulting mixture is then stirred at ice-water temperature for 2 h. The potassium salts are then removed via filtration and the filtrate is concentrated via rotovaping. The residue is then partitioned between $CH_2Cl_2$ and water. The product is then extracted into the $CH_2Cl_2$ layer, dried over sodium sulfate and concentrated to obtain 1-[4-[(4-fluorobenzoyl) amino]cyclohexyl]amine as a white solid.

Formulation Example

Tablets, each containing 50 mg of active ingredients, e.g., 1-[[(4-(benzoylamino)cyclohexyl]amino]acetyl]-2-cyano-(S)-pyrrolidine in free base form, can be prepared as follows:

| Composition (for 10,000 tablets) | |
|---|---|
| Active ingredient | 500.0 g |
| Lactose | 500.0 g |
| Potato starch | 352.0 g |
| Gelatin | 8.0 g |
| Talc | 60.0 g |
| Magnesium stearate | 10.0 g |
| Silica (highly disperse) | 20.0 g |
| Ethanol | q.s. |

The active ingredient is mixed with the lactose and 292 g of potato starch, and the mixture is moistened using an alcoholic solution of the gelatin and granulated by means of a sieve. After drying, the remainder of the potato starch, the talc, the magnesium stearate and the highly disperse silica are admixed and the mixture is compressed to give tablets of weight 145.0 mg each and active ingredient content 50.0 mg which, if desired, can be provided with breaking notches for finer adjustment of the dose.

What is claimed is:

1. A compound of formula I:

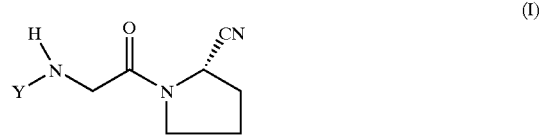

where Y is:

a) a group of the formula

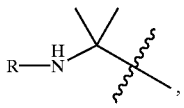

where R is an unsubstituted pyridine or pyrimidine ring; a pyridine or pyrimidine ring which is mono- or independently di-substituted by halo, trifluoromethyl, cyano, nitro or $C_{1-6}$alkyl; unsubstituted benzoyl; a benzoyl group which is mono- or di-substituted by halo or $C_{1-6}$alkyl; $C_{1-6}$alkylcarbonyl; di-$C_{1-6}$alkylaminocarbonyl; unsubstituted phenylaminocarbonyl; or a phenylaminocarbonyl group which is mono- or di-substituted on the phenyl ring by halo or $C_{1-6}$alkyl;

b) a group of the formula

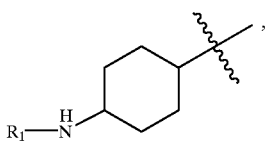

where $R_1$ is an unsubstituted pyridine, pyrimidine or phenyl ring; a pyridine, pyrimidine or phenyl ring which is mono- or independently di-substituted by halo, trifluoromethyl, cyano, nitro or $C_{1-6}$alkyl; an unsubstituted phenylsulfonyl group; a phenylsulfonyl group which is mono- or di-substituted on the phenyl ring by halo, trifluoromethyl, cyano, nitro or $C_{1-6}$alkyl; unsubstituted benzoyl; a benzoyl group which is mono- or di-substituted by halo or $C_{1-6}$alkyl; $C_{1-6}$alkylcarbonyl; thienyl sulfonyl; unsubstituted benzothiazole; or a benzothiazole group which is substituted on the phenyl ring by halo or $C_{1-6}$alkyl;

c) a group of the formula

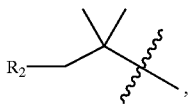

where $R_2$ is an unsubstituted phenyl ring; or a phenyl ring which is mono- or di-substituted by halo or $C_{1-6}$alkyl;

d) a group of the formula

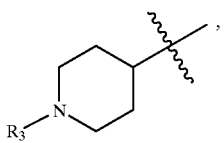

where $R_3$ is an unsubstituted phenylsulfonyl group; a phenylsulfonyl group which is mono- or di-substituted on the phenyl ring by halo, trifluoromethyl, cyano, nitro or $C_{1-6}$alkyl; $C_{1-6}$alkylcarbonyl; di-$C_{1-6}$alkylaminocarbonyl; $C_{3-8}$cycloalkylcarbonyl; unsubstituted benzoyl; a benzoyl group which is mono- or di-substituted by halo or $C_{1-6}$alkyl; unsubstituted phenylaminocarbonyl; phenylaminocarbonyl which is mono- or di-substituted on the phenyl ring by halo or $C_{1-6}$alkyl; a phenyl-substituted thiazole ring; or a phenyl-substituted thiazole ring wherein the phenyl ring is mono- or di-substituted by halo or $C_{1-6}$alkoxy;

e) a (4-pentylbicyclo[2.2.2]oct-1-yl)amine group; or f) a group of the formula

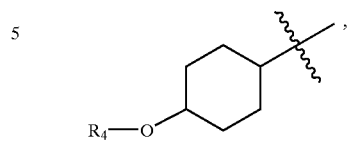

where $R_4$ is an unsubstituted phenyl ring; or a phenyl ring which is mono- or di-substituted by halo, trifluoromethyl, cyano, nitro or $C_{1-6}$alkyl;

and wherein the bond containing the wavy line signifies the point of attachment of the "Y" group to the glycyl-2-cyanopyrrolidine moiety;

or an acid addition salt thereof.

2. A compound according to claim 1 of formula Ia:

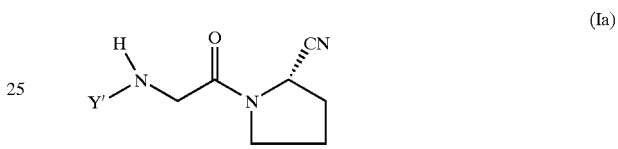

(Ia)

where Y' is:

a) a group of the formula

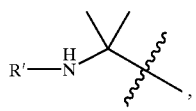

where R' is an unsubstituted pyridine or pyrimidine ring; a pyridine or pyrimidine ring which is mono- or independently di-substituted by halo, trifluoromethyl or cyano; unsubstituted benzoyl; a benzoyl group which is monosubstituted by halo or $C_{1-6}$alkyl; $C_{1-6}$alkylcarbonyl; di-$C_{1-6}$alkylaminocarbonyl; unsubstituted phenylaminocarbonyl; or a phenylaminocarbonyl group which is monosubstituted on the phenyl ring by halo or $C_{1-6}$alkyl;

b) a group of the formula II

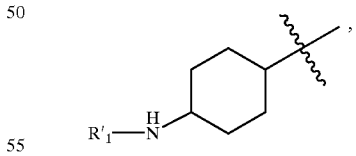

where $R_1'$ is an unsubstituted pyridine, pyrimidine or phenyl ring; a pyridine, pyrimidine or phenyl ring which is mono-substituted by halo, trifluoromethyl, cyano, nitro or $C_{1-6}$alkyl; an unsubstituted phenylsulfonyl group; a phenylsulfonyl group which is monosubstituted on the phenyl ring by halo, trifluoromethyl, cyano, nitro or $C_{1-6}$alkyl; unsubstituted benzoyl; a benzoyl group which is monosubstituted by halo or $C_1$alkyl; $C_{1-6}$alkylcarbonyl; thienyl sulfonyl; unsubstituted benzothiazole; or a benzothiazole group which is substituted on the phenyl ring by halo or $C_{1-6}$alkyl;

c) a group of the formula

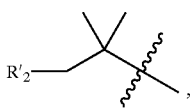

where $R_2'$ is an unsubstituted phenyl ring; or a phenyl ring which is monosubstituted by halo or $C_{1-6}$alkyl;

d) a group of the formula

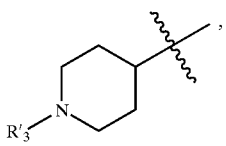

where $R_3'$ is an unsubstituted phenylsulfonyl group; a phenylsulfonyl group which is monosubstituted on the phenyl ring by halo, trifluoromethyl, cyano, nitro or $C_{1-6}$alkyl; $C_{1-6}$alkylcarbonyl; di-$C_{1-6}$alkylaminocarbonyl; $C_{3-8}$cycloalkylcarbonyl; unsubstituted benzoyl; a benzoyl group which is monosubstituted by halo or $C_{1-6}$alkyl; unsubstituted phenylaminocarbonyl; phenylaminocarbonyl which is monosubstituted on the phenyl ring by halo or $C_{1-6}$alkyl; a phenyl-substituted thiazole ring; or a phenyl-substituted thiazole ring wherein the phenyl ring is monosubstituted by halo or $C_{1-6}$alkoxy;

e) a (4-pentylbicyclo[2.2.2]oct-1-yl)amine group; or f) a group of the formula

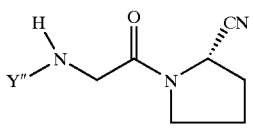

where $R_4'$ is an unsubstituted phenyl ring; or a phenyl ring which is monosubstituted by halo, trifluoromethyl, cyano, nitro or $C_{1-6}$alkyl;

or an acid addition salt thereof.

3. A compound according to claim 2 of formula Ib:

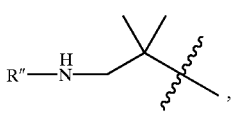

(Ib)

where Y" is:

a) a group of the formula

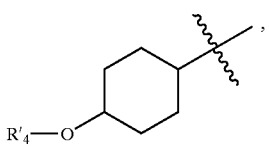

where R'" is an unsubstituted pyridine or pyrimidine ring; a pyridine or pyrimidine ring which is mono-substituted by halo, trifluoromethyl or cyano or di-substituted by halo; unsubstituted benzoyl; a benzoyl group which is monosubstituted by halo or $C_{1-4}$alkyl; $C_{1-6}$alkylcarbonyl; di-$C_{1-6}$alkylaminocarbonyl; unsubstituted phenylaminocarbonyl; or a phenylaminocarbonyl group which is monosubstituted on the phenyl ring by halo or $C_{1-4}$alkyl;

b) a group of the formula

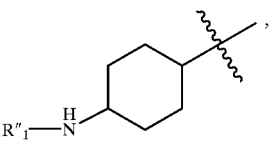

where $R_1''$ is an unsubstituted pyridine, pyrimidine or phenyl ring; a pyridine, pyrimidine or phenyl ring which is monosubstituted by halo, trifluoromethyl, cyano, nitro or $C_{1-4}$alkyl; an unsubstituted phenylsulfonyl group; a phenylsulfonyl group which is monosubstituted on the phenyl ring by halo, trifluoromethyl, cyano, nitro or $C_{1-4}$alkyl; unsubstituted benzoyl; a benzoyl group which is monosubstituted by halo or $C_{1-4}$alkyl; $C_{1-6}$alkylcarbonyl; thienyl sulfonyl; unsubstituted benzothiazole; or a benzothiazole group which is substituted on the phenyl ring by halo or $C_{1-4}$alkyl;

c) a group of the formula

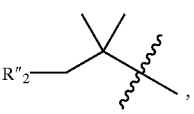

where $R_2''$ is an unsubstituted phenyl ring; or a phenyl ring which is monosubstituted by halo or $C_{1-4}$alkyl;

d) a group of the formula

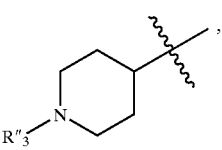

where $R_3''$ is an unsubstituted phenylsulfonyl group; a phenylsulfonyl group which is monosubstituted on the phenyl ring by halo, trifluoromethyl, cyano, nitro or $C_{1-4}$alkyl; $C_{1-6}$alkylcarbonyl; di-$C_{1-6}$alkylaminocarbonyl; $C_{3-8}$cycloalkylcarbonyl; unsubstituted benzoyl; a benzoyl group which is monosubstituted by halo or $C_{1-4}$alkyl; unsubstituted phenylaminocarbonyl; phenylaminocarbonyl which is monosubstituted on the phenyl ring by halo or $C_{1-4}$alkyl; a phenyl-substituted thiazole ring; or a phenyl-substituted thiazole ring wherein the phenyl ring is monosubstituted by halo or $C_{1-4}$alkoxy;

e) a (4-pentylbicyclo[2.2.2]oct-1-yl)amine group; or f) a group of the formula

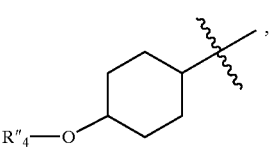

where $R_4''$ is an unsubstituted phenyl ring; or a phenyl ring which is monosubstituted by halo, trifluoromethyl, cyano, nitro or $C_{1-4}$alkyl;

or an acid addition salt thereof.

4. A compound according to claim 3 of formula Ic:

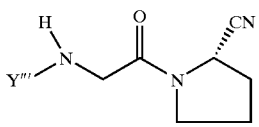
(Ic)

where Y''' is:

a) a group of the formula

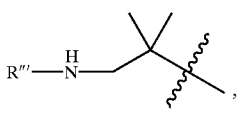

where R''' is an unsubstituted pyridine or pyrimidine ring; a pyridine or pyrimidine ring which is monosubstituted by chloro, trifluoromethyl or cyano or disubstituted by chloro; unsubstituted benzoyl; a benzoyl group which is monosubstituted by chloro, methyl or ethyl; $C_{1-6}$alkylcarbonyl; di-$C_{1-6}$alkylaminocarbonyl; unsubstituted phenylaminocarbonyl; or a phenylaminocarbonyl group which is monosubstituted on the phenyl ring by chloro;

b) a group of the formula

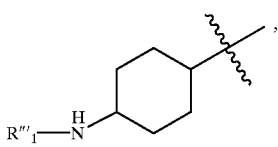

where $R_1'''$ is an unsubstituted pyridine, pyrimidine or phenyl ring; a pyridine, pyrimidine or phenyl ring which is monosubstituted by chloro, trifluoromethyl or cyano; an unsubstituted phenylsulfonyl group; a phenylsulfonyl group which is monosubstituted on the phenyl ring by chloro or trifluoromethyl; unsubstituted benzoyl; a benzoyl group which is monosubstituted by chloro; $C_{1-6}$alkylcarbonyl; thienyl sulfonyl; unsubstituted benzothiazole; or a benzothiazole group which is substituted on the phenyl ring by chloro;

c) a group of the formula

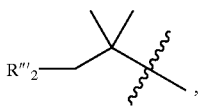

where $R_2'''$ is an unsubstituted phenyl ring; or a phenyl ring which is monosubstituted by fluoro;

d) a group of the formula

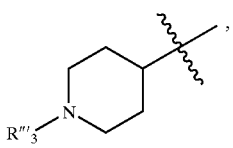

where $R_3'''$ is an unsubstituted phenylsulfonyl group; a phenylsulfonyl group which is monosubstituted on the phenyl ring by chloro or trifluoromethyl; $C_{1-6}$alkylcarbonyl; di-$C_{1-6}$alkylaminocarbonyl; $C_{3-8}$cycloalkylcarbonyl; unsubstituted benzoyl; a benzoyl group which is monosubstituted by chloro; unsubstituted phenylaminocarbonyl; phenylaminocarbonyl which is monosubstituted on the phenyl ring by chloro; a phenyl-substituted thiazole ring; or a phenyl-substituted thiazole ring wherein the phenyl ring is monosubstituted by chloro or methoxy;

e) a (4-pentylbicyclo[2.2.2]oct-1-yl)amine group; or f) a group of the formula

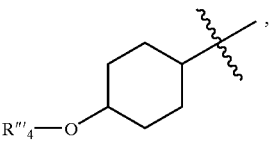

where $R_4'''$ is an unsubstituted phenyl ring; or a phenyl ring which is monosubstituted by chloro or trifluoromethyl;

or an acid addition salt thereof.

5. The compound according to claim 1 which is selected from the group consisting of 1-[[[4-(benzoylamino)cyclohexyl]amino]acetyl]-2-cyano-(S)-pyrrolidine, 1-[[[1-[(4-chlorophenyl)sulfonyl]-4-piperidinyl]amino]acetyl]-2-cyano-(S)-pyrrolidine, and 1-[[[4-[(4-fluorobenzoyi)amino]cyclohexyl]amino]acetyl]-2-cyano-(S)-pyrrolidine, or, in each case, an acid addition salt thereof.

6. A compound according to claim 5 in free base form.

7. A pharmaceutical composition comprising a pharmaceutically acceptable carrier or diluent and a therapeutically effective amount of a compound according to claim 1, or a pharmaceutically acceptable acid addition salt thereof.

8. A pharmaceutical composition comprising a pharmaceutically acceptable carrier or diluent and a therapeutically effective amount of a compound according to claim 2, or a pharmaceutically acceptable acid addition salt thereof.

9. A pharmaceutical composition comprising a pharmaceutically acceptable carrier or diluent and a therapeutically effective amount of a compound according to claim 3, or a pharmaceutically acceptable acid addition salt thereof.

10. A pharmaceutical composition comprising a pharmaceutically acceptable carrier or diluent and a therapeutically effective amount of a compound according to claim 4, or a pharmaceutically acceptable acid addition salt thereof.

11. A pharmaceutical composition according to claim 7 wherein the compound is selected from the group consisting of 1-[[[4-(benzoylamino)cyclohexyl]amino]acetyl]-2-cyano-(S)-pyrrolidine, 1-[[[1-[(4-chlorophenyl)sulfonyl]-4-piperidinyl]amino]acetyl]-2-cyano-(S)-pyrrolidine, and 1-[[[4-[(4-fluorobenzoyl)amino]cyclohexyl]amino]acetyl]-2-cyano-(S)-pyrrolidine, or, in each case, an acid addition salt thereof.

12. A pharmaceutical composition according to claim 11 wherein the compound is in free base form.

13. A method of inhibiting dipeptidyl peptidase-IV comprising administering to a mammal in need of such treatment a therapeutically effective amount of a compound according to claim 1, or a pharmaceutically acceptable acid addition salt thereof.

14. A method of inhibiting dipeptidyl pepidase-IV comprising administering to a mammal in need of such treatment a therapeutically effective amount of a compound according to claim 2, or a pharmaceutically acceptable acid addition salt thereof.

15. A method of inhibiting dipeptidyl pepidase-IV comprising administering to a mammal in need of such treatment a therapeutically effective amount of a compound according to claim 3, or a pharmaceutically acceptable acid addition salt thereof.

16. A method of inhibiting dipeptidyl pepidase-IV comprising administering to a mammal in need of such treatment a therapeutically effective amount of a compound according to claim 4, or a pharmaceutically acceptable acid addition salt thereof.

17. A method according to claim 13 wherein the compound administered is selected from the group consisting of 1-[[[4-(benzoylamino)cyclohexyl]amino]acetyl]-2-cyano-(S)-pyrrolidine, 1-[[[1-[(4-chlorophenyl)sulfonyl]-4-piperidinyl]amino]acetyl]-2-cyano-(S)-pyrrolidine, and 1-[[[4-[(4-fluorobenzoyl)amino]cyclohexyl]amino]acetyl]-2-cyano-(S)-pyrrolidine, or, in each case, an acid addition salt thereof.

18. A method according to claim 17 wherein the compound administered is in free base form.

19. A method of treating conditions mediated by dipeptidyl peptidase-IV inhibition comprising administering to a mammal in need of such treatment a therapeutically effective amount of a compound according to claim 1, or a pharmaceutically acceptable acid addition salt thereof.

20. A method of treating conditions mediated by dipeptidyl peptidase-IV inhibition comprising administering to a mammal in need of such treatment a therapeutically effective amount of a compound according to claim 2, or a pharmaceutically acceptable acid addition salt thereof.

21. A method of treating conditions mediated by dipeptidyl peptidase-IV inhibition comprising administering to a mammal in need of such treatment a therapeutically effective amount of a compound according to claim 3, or a pharmaceutically acceptable acid addition salt thereof.

22. A method of treating conditions mediated by dipeptidyl peptidase-IV inhibition comprising administering to a mammal in need of such treatment a therapeutically effective amount of a compound according to claim 4, or a pharmaceutically acceptable acid addition salt thereof.

23. A method according to claim 19 wherein the compound administered is selected from the group consisting of 1-[[[4-(benzoylamino)cyclohexyl]amino]acetyl]-2-cyano-(S)-pyrrolidine, 1-[[[1-[(4-chlorophenyl)sulfonyl]-4-piperidinyl]amino]acetyl]-2-cyano-(S)pyrrolidine, and 1-[[[4-[(4-fluorobenzoyl)amino]cyclohexyl]amino]acetyl]-2-cyano-(S)-pyrrolidine, or, in each case, an acid addition salt thereof.

24. A method according to claim 23 wherein the compound administered is in free base form.

25. A method according to claim 19 wherein the condition treated is non-insulin-dependent diabetes mellitus.

26. A method according to claim 20 wherein the condition treated is non-insulin-dependent diabetes mellitus.

27. A method according to claim 21 wherein the condition treated is non-insulin-dependent diabetes mellitus.

28. A method according to claim 22 wherein the condition treated is non-insulin-dependent diabetes mellitus.

29. A method according to claim 23 wherein the condition treated is non-insulin-dependent diabetes mellitus.

30. A method according to claim 24 wherein the condition treated is non-insulin dependent diabetes mellitus.

31. A compound according to claim 1 selected from formulae

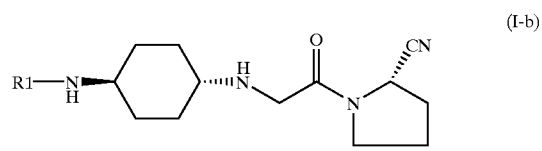

(I-b)

and

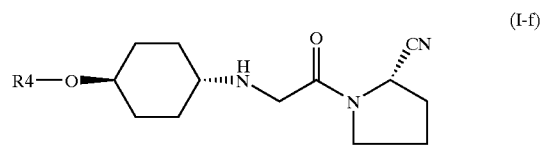

(I-f)

* * * * *

UNITED STATES PATENT AND TRADEMARK OFFICE
CERTIFICATE OF CORRECTION

PATENT NO. : 6,432,969 B1
DATED : August 13, 2002
INVENTOR(S) : Edwin Bernard Villhauer It is certified that error appears in the above-identified patent and that said Letters Patent is hereby corrected as shown below:

Column 30,
Line 65, should read:
-- by halo or $C_{1-6}$alkyl; $C_{1-6}$alkylcarbonyl; thienyl sulfonyl; --

Signed and Sealed this

Twenty-sixth Day of November, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO.    : 6,432,969 B1  
DATED         : August 13, 2002  
INVENTOR(S)   : Edwin Bernard Villhauer Page 1 of 1

It is certified that error appears in the above-identified patent and that said Letters Patent is hereby corrected as shown below:

Column 2,  
Line 25, should read:

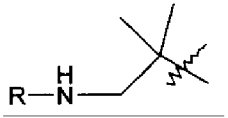

Column 6,  
Line 35, should read:

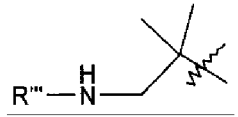

Column 29,  
Line 5, should read:

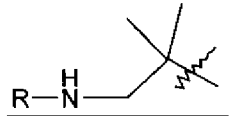

Column 30,  
Line 35, should read:

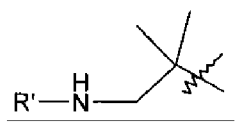

Signed and Sealed this

Second Day of August, 2005

JON W. DUDAS  
*Director of the United States Patent and Trademark Office*